United States Patent
Siegfried et al.

(10) Patent No.: US 10,047,374 B2
(45) Date of Patent: Aug. 14, 2018

(54) PARENTAL RNAI SUPPRESSION OF KRUPPEL GENE TO CONTROL HEMIPTERAN PESTS

(71) Applicants: Dow AgroSciences LLC, Zionsville, IN (US); The Board of Regents of the University of Nebraska, Lincoln, NE (US)

(72) Inventors: Blair D. Siegfried, Lincoln, NE (US); Kenneth E. Narva, Zionsville, IN (US); Kanika Arora, Indianapolis, IN (US); Sarah E. Worden, Indianapolis, IN (US); Chitvan Khajuria, Chesterfield, MO (US); Elane Fishilevich, Indianapolis, IN (US); Nicholas P. Storer, Kensington, MD (US); Meghan Frey, Greenwood, IN (US); Ronda L. Hamm, Carmel, IN (US); Ana Velez, Lincoln, NE (US)

(73) Assignees: Dow AgroSciences LLC, Indianapolis, IN (US); The Board of Regents of the University of Nebraska, Lincoln, NE (US)

( * ) Notice: Subject to any disclaimer, the term of this patent is extended or adjusted under 35 U.S.C. 154(b) by 95 days.

(21) Appl. No.: 14/971,550

(22) Filed: Dec. 16, 2015

(65) Prior Publication Data

US 2016/0369296 A1 Dec. 22, 2016

Related U.S. Application Data

(60) Provisional application No. 62/092,784, filed on Dec. 16, 2014.

(51) Int. Cl.
*C12N 15/82* (2006.01)
*C12N 15/113* (2010.01)
*A01N 57/16* (2006.01)

(52) U.S. Cl.
CPC ......... *C12N 15/8286* (2013.01); *A01N 57/16* (2013.01); *C12N 15/113* (2013.01); *C12N 15/8218* (2013.01); *C12N 15/8261* (2013.01); *C12N 2310/14* (2013.01)

(58) Field of Classification Search
CPC .................................................. C12N 15/8286
USPC ......................................................... 800/279
See application file for complete search history.

(56) References Cited

U.S. PATENT DOCUMENTS

| | | | |
|---|---|---|---|
| 2009/0188005 A1* | 7/2009 | Boukharov | ........ C07K 14/4354 800/279 |
| 2012/0174258 A1 | 7/2012 | Narva et al. | |
| 2013/0058890 A1 | 3/2013 | Raemaekers et al. | |

FOREIGN PATENT DOCUMENTS

WO  2007035650  3/2007

OTHER PUBLICATIONS

Thomas et al. 2001, The Plant Journal 25(4):417-425.*
Yibrah et al. 1993, Hereditas 118:273-2890.*
Baum, James, A. et al., "Control of coleopteran insect pests through RNA interference," Nature Biotechnology, pp. 1322-1326, Nov. 2007, vol. 25, No. 11.
International Search Report and Written Opinion for PCT/US2015/066010, dated Mar. 31, 2016.
International Search Report and Written Opinion for PCT/US2015/066034, dated Apr. 19, 2016.
Mito, Taro et al., "Kruppel acts as a gap gene regulating expression of hunchback and even-skipped in the intermediate germ cricket Gryllus bimaculatus," Developmental Biology, Epub. Apr. 17, 2006, pp. 471-481, vol. 294, No. 2.
NCBI, GenBank accession No. AY804656.1 (Oct. 4, 2005).
Palli, Subba Reddy, "RNAi methods for management of insects and their pathogens," CAB Reviews, Mar. 28, 2012, pp. 1-10, No. 4.

* cited by examiner

*Primary Examiner* — Li Zheng
(74) *Attorney, Agent, or Firm* — Sean M. Russell; Magleby Cataxinos & Greenwood

(57) ABSTRACT

This disclosure concerns nucleic acid molecules and methods of use thereof for control of hemipteran pests through RNA interference-mediated inhibition of target coding and transcribed non-coding sequences in hemipteran pests. The disclosure also concerns methods for making transgenic plants that express nucleic acid molecules useful for the control of hemipteran pests, and the plant cells and plants obtained thereby.

32 Claims, 4 Drawing Sheets

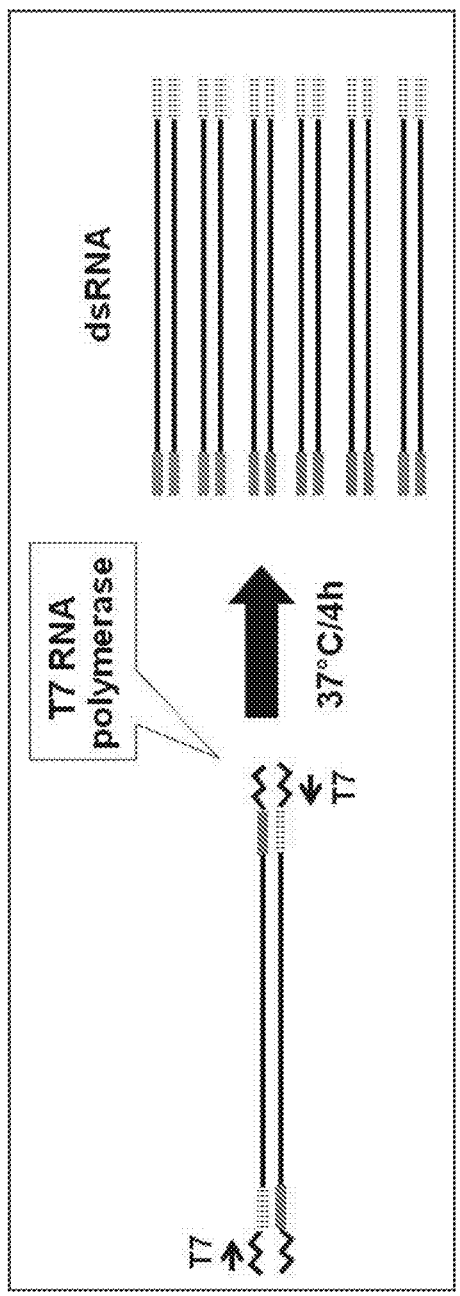 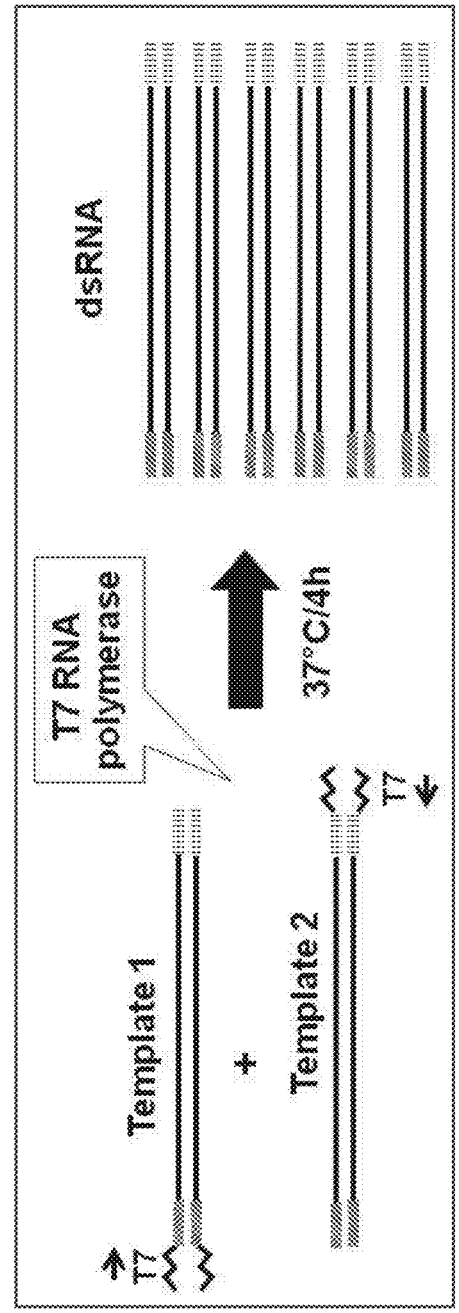
FIG. 1A
FIG. 1B

PARENTAL RNAI SUPPRESSION OF KRUPPEL GENE TO CONTROL HEMIPTERAN PESTS

PRIORITY CLAIM

This application claims the benefit of the filing date of U.S. Provisional Patent Application Ser. No. 62/092,784, filed Dec. 16, 2014, for "PARENTAL RNAI SUPPRESSION OF KRUPPEL GENE TO CONTROL HEMIPTERAN PESTS" which is incorporated herein in its entirety.

FIELD OF THE DISCLOSURE

The present invention relates generally to genetic control of plant damage caused by hemipteran pests. In particular embodiments, the present disclosure relates to identification of target coding and non-coding polynucleotides, and the use of recombinant DNA technologies for post-transcriptionally repressing or inhibiting expression of target coding and non-coding polynucleotides in the cells of a hemipteran pest to provide a plant protective effect.

BACKGROUND

Stink bugs and other hemipteran insects (heteroptera) are an important agricultural pest complex. Worldwide, over 50 closely related species of stink bugs are known to cause crop damage. McPherson & McPherson (2000) *Stink bugs of economic importance in America north of Mexico*, CRC Press. Hemipteran insects are present in a large number of important crops including maize, soybean, cotton, fruit, vegetables, and cereals.

Stink bugs go through multiple nymph stages before reaching the adult stage. These insects develop from eggs to adults in about 30-40 days. Both nymphs and adults feed on sap from soft tissues into which they also inject digestive enzymes causing extra-oral tissue digestion and necrosis. Digested plant material and nutrients are then ingested. Depletion of water and nutrients from the plant vascular system results in plant tissue damage. Damage to developing grain and seeds is the most significant as yield and germination are significantly reduced. Multiple generations occur in warm climates resulting in significant insect pressure. Current management of stink bugs relies on insecticide treatment on an individual field basis. Therefore, alternative management strategies are urgently needed to minimize ongoing crop losses.

RNA interference (RNAi) is a process utilizing endogenous cellular pathways, whereby an interfering RNA (iRNA) molecule (e.g., a double stranded RNA (dsRNA) molecule) that is specific for all, or any portion of adequate size, of a target gene results in the degradation of the mRNA encoded thereby. In recent years, RNAi has been used to perform gene "knockdown" in a number of species and experimental systems; for example, *Caenorhabditis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro inhibitory ribonucleic acids (miRNAs) are structurally very similar molecules that are cleaved from precursor molecules containing a polynucleotide "loop" connecting the hybridized passenger and guide strands, and they may be similarly incorporated into RISC. Post-transcriptional gene silencing occurs when the guide strand binds specifically to a complementary mRNA molecule and induces cleavage by Argonaute, the catalytic component of the RISC complex. This process is known to spread systemically throughout some eukaryotic organisms despite initially limited concentrations of siRNA and/or miRNA such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein. In insects, there are at least two DICER genes, where DICER1 facilitates miRNA-directed degradation by Argonautel. Lee et al. (2004) Cell 117 (1):69-81. DICER2 facilitates siRNA-directed degradation by Argonaute2. Id.

The overwhelming majority of sequences complementary to insect DNAs (such as, for example, the 9,000+ sequences identified in U.S. Pat. No. 7,612,194 and U.S. Patent Publication Nos. 2007/0050860, 2010/0192265, and 2011/0154545) do not provide a plant protective effect when used as dsRNA or siRNA. For example, Baum et al. (2007) Nature Biotechnology 25:1322-1326, describe the effects of inhibiting several Western corn rootworm (WCR) gene targets by RNAi. These authors reported that 8 of the 26 target genes they tested were not able to provide experimentally significant coleopteran pest mortality at a very high iRNA (e.g., dsRNA) concentration of more than 520 ng/cm$^2$.

The authors of U.S. Pat. No. 7,612,194 and U.S. Patent Publication No. 2007/0050860 made the first report of in planta RNAi in corn plants targeting the western corn rootworm. Baum et al. (2007) Nat. Biotechnol. 25(11):1322-6. These authors describe a high-throughput in vivo dietary RNAi system to screen potential target genes for developing transgenic RNAi maize. Of an initial gene pool of 290 targets, only 14 exhibited larval control potential. One of the most effective double-stranded RNAs (dsRNA) targeted a gene encoding vacuolar ATPase subunit A (V-ATPase), resulting in a rapid suppression of corresponding endogenous mRNA and triggering a specific RNAi response with low concentrations of dsRNA. Thus, these authors documented for the first time the potential for in planta RNAi as a possible pest management tool, while simultaneously demonstrating that effective targets could not be accurately identified a priori, even from a relatively small set of candidate genes.

Another potential application of RNAi for insect control involves parental RNAi (pRNAi). First described in *Caenorhabditis elegans*, pRNAi was identified by injection of dsRNA into the body cavity (or application of dsRNA via ingestion), causing gene inactivity in offspring embryos. Fire et al. (1998), supra; Timmons and Fire (1998) Nature 395(6705):854. A similar process was described in the model coleopteran, Tribolium castaneum, whereby female pupae injected with dsRNA corresponding to three unique genes that control segmentation during embryonic development resulted in knock down of zygotic genes in offspring embryos. Bucher et al. (2002) Curr. Biol. 12(3):R85-6. Nearly all of the offspring larvae in this study displayed gene-specific phenotypes one week after injection. Although injection of dsRNA for functional genomics studies has been successful in a variety of insects, uptake of dsRNA from the gut environment through oral exposure to dsRNA and subsequent down-regulation of essential genes is required in order for RNAi to be effective as a pest management tool. Auer and Frederick (2009) Trends Biotechnol. 27(11):644-51.

Parental RNAi has been used to describe the function of embryonic genes in a number of insect species, including the springtail, *Orchesella cincta* (Konopova and Akam (2014) Evodevo 5(1):2); the brown plant hopper, *Nilaparvata lugens*; the sawfly, *Athalia rosae* (Yoshiyama et al. (2013) J. Trisect Physiol. 59(4):400-7); the German cockroach, *Blattella germanica* (Piulachs et al. (2010) Trisect Biochem. Mol. Biol. 40:468-75); and the pea aphid, *Acyrthosiphon pisum* (Mao et al. (2013) Arch Trisect Biochem Physiol 84(4):209-21). The pRNAi response in all these instances was achieved by injection of dsRNA into the hemocoel of the parental female.

SUMMARY OF THE DISCLOSURE

Disclosed herein are nucleic acid molecules (e.g., target genes, DNAs, dsRNAs, siRNAs, shRNAs, miRNAs, and hpRNAs), and methods of use thereof, for the control of hemipteran pests, including, for example, *Euschistus heros* (Fabr.) (Neotropical Brown Stink Bug, "BSB"); *E. serous* (Say) (Brown Stink Bug); *Nezara viridula* (L.) (Southern Green Stink Bug); *Piezodorus guildinii* (Westwood) (Redbanded Stink Bug); *Halyomorpha halys* (Stal) (Brown Marmorated Stink Bug); *Chinavia hilare* (Say) (Green Stink Bug); *C. marginatum* (Palisot de Beauvois); *Dichelops melacanthus* (Dallas); *D. furcatus* (F.); *Edessa meditabunda* (F.); *Thyanta perditor* (F.) (Neotropical Red Shouldered Stink Bug); *Horcias nobilellus* (Berg) (Cotton Bug); *Taedia stigmosa* (Berg); *Dysdercus peruvianus* (Guérin-Méneville); *Neomegalotomus parvus* (Westwood); *Leptoglossus zonatus* (Dallas); *Niesthrea sidae* (F.); *Lygus hesperus* (Knight) (Western Tarnished Plant Bug); and *L. lineolaris* (Palisot de Beauvois). In particular examples, exemplary nucleic acid molecules are disclosed that may be homologous to at least a portion of one or more native nucleic acids in a hemipteran pest. In some embodiments, hemipteran pests are controlled by reducing the capacity of an existing generation of the pest to produce a subsequent generation of the pest. In certain examples, delivery of the nucleic acid molecules to hemipteran pests does not result in significant mortality to the pests, but reduces the number of viable progeny produced therefrom.

In these and further examples, the native nucleic acid may be a target gene, the product of which may be, for example and without limitation: involved in a metabolic process; involved in a reproductive process; and/or involved in embryonic and/or nymph development. In some examples, post-transcriptional inhibition of the expression of a target gene by a nucleic acid molecule comprising a polynucleotide homologous thereto may result in reduced growth and/or reproduction of the hemipteran pest. In specific examples, a kruppel gene is selected as a target gene for post-transcriptional silencing. In particular examples, a target gene useful for post-transcriptional inhibition is the novel gene referred to herein as BSB kruppel (SEQ ID NO:1), referred to herein in some places as BSB_kr. An isolated nucleic acid molecule comprising the polynucleotide of SEQ ID NO:1; the complement of SEQ ID NO:1; and/or fragments of either of the foregoing (e.g., SEQ ID NO:3 and SEQ ID NO:4) is therefore also disclosed herein.

Also disclosed are nucleic acid molecules comprising a polynucleotide that encodes a polypeptide that is at least about 85% identical to an amino acid sequence within a target gene product (for example, the product of a kruppel gene). For example, a nucleic acid molecule may comprise a polynucleotide encoding a polypeptide that is at least 85% identical to SEQ ID NO:2 (BSB KRUPPEL); and/or an amino acid sequence within a product of BSB_kr. Further disclosed are nucleic acid molecules comprising a polynucleotide that is the reverse complement of a polynucleotide that encodes a polypeptide at least 85% identical to an amino acid sequence within a target gene product.

Additionally disclosed are cDNA polynucleotides that may be used for the production of iRNA (e.g., dsRNA, siRNA, shRNA, miRNA, and hpRNA) molecules that are complementary to all or part of a hemipteran pest target gene, for example, a kruppel gene. In particular embodiments, dsRNAs, siRNAs, shRNAs, miRNAs, and/or hpRNAs may be produced in vitro, or in vivo by a genetically-modified organism, such as a plant or bacterium. In particular examples, cDNA molecules are disclosed that may be used to produce iRNA molecules that are complementary to all or part of mRNA transcribed from BSB_kr (SEQ ID NO:1).

Further disclosed are means for inhibiting expression of an essential gene in a hemipteran pest, and means for protecting a plant from a hemipteran pest. A means for inhibiting expression of an essential gene in a hemipteran pest is a single- or double-stranded RNA molecule consisting of a polynucleotide selected from the group consisting of SEQ ID NO:15, SEQ ID NO:16, and SEQ ID NO:17; and the complements of the foregoing. Functional equivalents of means for inhibiting expression of an essential gene in a hemipteran pest include single- or double-stranded RNA molecules that are substantially homologous to all or part of mRNA transcribed from a BSB gene comprising SEQ ID NO:1. A means for protecting a plant from a hemipteran pest is a DNA molecule comprising a polynucleotide encoding a means for inhibiting expression of an essential gene in a hemipteran pest operably linked to a promoter, wherein the DNA molecule is capable of being integrated into the genome of a maize plant.

Disclosed are methods for controlling a population of a hemipteran pest, comprising providing to a hemipteran pest an iRNA (e.g., dsRNA, siRNA, shRNA, miRNA, and hpRNA) molecule that functions upon being taken up by the pest to inhibit a biological function within the pest, wherein the iRNA molecule comprises all or part of (e.g., at least 15 contiguous nucleotides of) a polynucleotide selected from the group consisting of: SEQ ID NO:1; the complement of SEQ ID NO:1; SEQ ID NO:3; the complement of SEQ ID NO:3; SEQ ID NO:4; the complement of SEQ ID NO:4; a native coding polynucleotide of a hemipteran organism (e.g., BSB) comprising all or part of SEQ ID NO:1; the complement of a native coding polynucleotide of a hemipteran organism comprising all or part of SEQ ID NO:1; a native non-coding polynucleotide of a hemipteran organism that is transcribed into a native RNA molecule comprising all or part of SEQ ID NO:15; and the complement of a native non-coding polynucleotide of a hemipteran organism that is transcribed into a native RNA molecule comprising all or part of SEQ ID NO:15.

In particular examples, methods are disclosed for controlling a population of a hemipteran pest, comprising providing to a hemipteran pest an iRNA (e.g., dsRNA, siRNA, shRNA, miRNA, and hpRNA) molecule that functions upon being taken up by the pest to inhibit a biological function within the pest, wherein the iRNA molecule comprises a polynucleotide selected from the group consisting of all or part of: SEQ ID NO:15; the complement of SEQ ID NO:15; SEQ ID NO:16; the complement of SEQ ID NO:16; SEQ ID NO:17; the complement of SEQ ID NO:17; a polynucleotide that hybridizes to a native coding polynucleotide of a hemipteran (e.g., BSB) organism comprising all or part of SEQ ID NO:1; and the complement of a polynucleotide that hybridizes to a native coding polynucleotide of a hemipteran (e.g., BSB) organism comprising all or part of SEQ ID NO:1.

Also disclosed herein are methods wherein dsRNAs, siRNAs, shRNAs, miRNAs, and/or hpRNAs may be provided to a hemipteran pest in a diet-based assay, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by a hemipteran pest. Ingestion of dsRNAs, siRNA, shRNAs, miRNAs, and/or hpRNAs of the invention may then result in RNAi in the pest, which in turn may result in silencing of a gene essential for a metabolic process; a reproductive process; and/or nymph development. Thus, methods are disclosed wherein nucleic acid molecules comprising exemplary polynucleotide(s) useful for parental control of hemipteran pests are provided to a hemipteran pest. In particular examples, the hemipteran pest controlled by use of nucleic acid molecules of the invention may be BSB. In some examples, delivery of the nucleic acid molecules to hemipteran pests does not result in significant mortality to the pests, but reduces the number of viable progeny produced therefrom. In some examples, delivery of the nucleic acid molecules to hemipteran pests results in significant mortality to the pests, and also reduces the number of viable progeny produced therefrom.

The foregoing and other features will become more apparent from the following Detailed Description of several embodiments, which proceeds with reference to the accompanying Figures.

BRIEF DESCRIPTION OF THE FIGURES

FIG. 1 includes a depiction of the strategy used to generate dsRNA from a single transcription template with a single pair of primers (FIG. 1A), and from two transcription templates (FIG. 1B).

SEQUENCE LISTING

Figure 2:
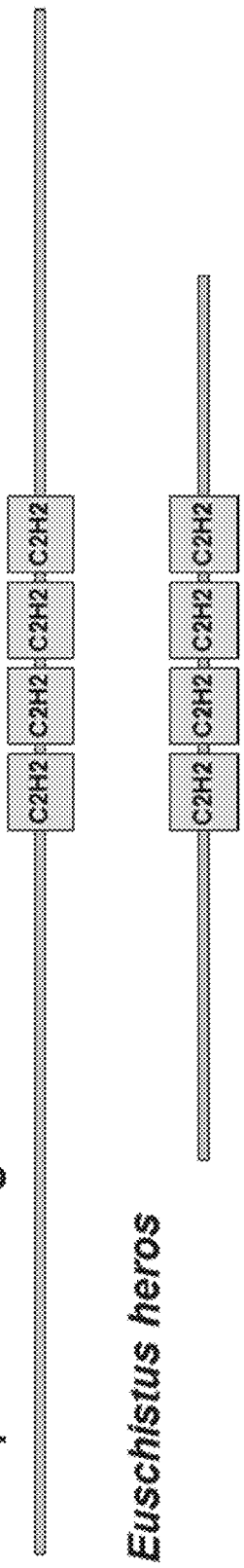
FIG. 2 includes a depiction of the domain organization of the *Drosophila melanogaster* (DME) and *Euschistus heros* (BSB) KRUPPEL protein sequences. *D. melanogaster* and *E. heros* KRUPPEL proteins contain four C2H2-type zinc fingers, annotated using SMART database within InterProScan.

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NO:1 shows an exemplary *E. heros* kruppel DNA, referred to herein in some places as BSB_kr:

AGGAGCAATAATCTCAATTTCTGAATTTTTTTACTTAAACCACTTTCATT

CTCACCGGCTCAATTATAGTTAAAAATCAGCTGATATATTTTCACTGATA

TAACCCAACCTGATTAACTTAAACACTTAAGTAATAATTACAAGAATTAA

CGGTTAGAGAGTTACTCAAACAAATTTTGTAAAATCTTATCAAACATTGA

TCGAAAAGCCACACAAATATCAACTACTAAATAACATCAACCAAAGTGAT

TGATTATCATAAAATTTTGTTGTTTTATTAAATGGGAAAAAAATAAATTT

TTGAAATCCATAAAAGAGCATAGGGGCATAGAGATGTTAAACAATAAAAA

GCGGAATTTTGCATCTGTCGGTTGGGTAAATTTTACAATATACATTCCAA

TAATAATTATTCCCAGAGATAACCTAATATCAAGTTTCCAGTCACTCTGA

CGTGGAATCACATGTTTTCATTTGAGAAACATACACGCTCAAAAATAGCG

CTTCCATCAATTAAAATATACACAACGAACTTATACTCTAATAATAATAT

ATAATAGAAAACAAAATAAATGAAATGACTATACCGAAACCGGTACATAC

CCGTAGTCGTTTTTACAGTACCTTCAGTAACCCTTACTATATTTCAAAAA

-continued

TCATAACTTCAATTATTACATCAATCCAGATCAAGAAATTGTACTCTAAA

ATAAGATATTTTAAATTTATTAATTTATGTACAATAAATCAATTTCGTTT

CGTACCTTATGACGTTAAAGCATTCAAATGGTATAGGGCACTGGCGGTAC

TGTGATAAAAAAATAATAATTTACTAACTAAAGAGGTGAGCCTCCATCCC

ATTCTTCAGAAAGCTCTTCTTCAGATTCAGTCATTGTGAGATTATTATTA

TTGTTGATGTTTTTGTTCTTATGCCTGATAGAAAGATCTTCAGGTTCGGT

CTGCTCAGGCAACGAAAGGTACGCAGGGATAACGTTTACAAGAGCTTGCG

CTTTTCTGTCCCTCGAGTCGCACTTGTGATGCAGGAGGTGGTGTCTCCTT

CTGAATTTGGCACCGCACAATCCGCAGCCGAATGGTTTTTCTCCCTTGTG

AATTAGAGAATGGGCCTTGAGCTGGTTGGAATCAGCGAACCTCGAGGAAC

AGACTTGGCAAGCGTAAGGCCGTTCTCCGGTATGTACCCGTAGGTGTCTC

CTCAAGTTGGCTACTTGCACGAAGTACCTGTCGCAGTGGTCGCAATGGTA

AGGCTTCTCGCCAGTGTGTGTGCGTATGTGGGTGCGGAGATGGTGGTCCC

GTCGAAACCTTCTGTGGCACTCGGGGCACTCGAACGGCCGTTCTCCAGTG

TGGGTTCTTTCGTGATTTTTGAGAACGTGCTTATGCTTGAAGGACTGGTT

ACAAGTGAGGCAGACGAAAGCTCTGTCCCTCCCAGGAGGAGAGTCTTCGT

CCTTCTTCTTCCTCCCTACAGGCTCTGGAGGTGGAGCTGCCCAGAGCAAA

GAGTGCGAGAATAGGGAGCCGCCTCCGATCCCGTGGAGAGCCAAAAGTCC

TGGCATTCCGGCTGCCAGAAGACCGGCCTCTGGACCGTTTTCTTCTCGTT

TGCTTGCTTCCTTCATTGTGCACCTTCCGACGCCTACTACTGAAGTCAAG

CCCTTGGTTGGGTTGTTGGTTGCGTGTATGAGAGACAAGGCCATGGAGGT

GTTATAGAGACGAAGGCATGGCAGGAAC

SEQ ID NO:2 shows the amino acid sequence of a *E. heros* KRUPPEL polypeptide encoded by an exemplary *E. heros* kruppel DNA:

MALSLIHATNNPTKGLTSVVGVGRCTMKEASKREENGPEAGLLAAGMPGL

LALHGIGGGSLFSHSLLWAAPPPEPVGRKKKDEDSPPGRDRAFVCLTCNQ

SFKHKHVLKNHERTHTGERPFECPECHRRFRRDHHLRTHIRTHTGEKPYH

CDHCDRYFVQVANLRRHLRVHTGERPYACQVCSSRFADSNQLKAHSLIHK

GEKPFGCGLCGAKFRRRHHLLHHKCDSRDRKAQALVNVIPAYLSLPEQTE

PEDLSIRHKNKNINNNNNLTMTESEEELSEEWDGGSPL

SEQ ID NO:3 shows an exemplary *E. heros* kruppel DNA (BSB_kr-1), of which the complementary strand is transcribed to become the sense strand of an exemplary BSB kruppel dsRNA:

GAGCTTGCGCTTTTCTGTCCCTCGAGTCGCACTTGTGATGCAGGAGGTGG

TGTCTCCTTCTGAATTTGGCACCGCACAATCCGCAGCCGAATGGTTTTTC

TCCCTTGTGAATTAGAGAATGGGCCTTGAGCTGGTTGGAATCAGCGAACC

TCGAGGAACAGACTTGGCAAGCGTAAGGCCGTTCTCCGGTATGTACCCGT

AGGTGTCTCCTCAAGTTGGCTACTTGCACGAAGTACCTGTCGCAGTGGTC

GCAATGGTAAGGCTTCTCGCCAGTGTGTGTGCGTATGTGGGTGCGGAGAT

-continued

GGTGGTCCCGTCGAAACCTTCTGTGGCACTCGGGGCACTCGAACGGCCGT

TCTCCAGTGTGGGTTCTTTCGTGATTTTTGAGAACGTGCTTATGCTTGAA

GGACTGGTTACAAGTGAGGCAGACGAAAGCTCTG

SEQ ID NO:4 shows an exemplary *E. heros* kruppel DNA (BSB_kr-2), of which the complementary strand is transcribed to become the sense strand of a further exemplary BSB kruppel dsRNA:

AAACATTGATCGAAAAGCCACACAAATATCAACTACTAAATAACATCAAC

CAAAGTGATTGATTATCATAAAATTTTGTTGTTTTATTAAATGGGAAAAA

AATAAATTTTTGAAATCCATAAAAGAGCATAGGGGCATAGAGATGTTAAA

CAATAAAAAGCGGAATTTTGCATCTGTCGGTTGGGTAAATTTTACAATAT

ACATTCCAATAATAATTATTCCCAGAGATAACCTAATATCAAGTTTCCAG

TCACTCTGACGTGGAATCACATGTTTTCATTTGAGAAACATACACGCTCA

AAAATAGCGCTTCCATCAATTAAAATATACACAACGAACTTATACTCTAA

TAATAATATATAATAGAAAACAAAATAAATGAAATGACTATACCGAAACC

GGTACATACCCGTAGTCGTTTTTACAGTACCTTCAGTAACCCTTACTATA

TTTCAAAAATCATAACTTCAATTATTACATCAATCCAGATCAAGAAATTG

TACTCTAAAATAAGATATTTTAAATTTATTAATTTATGTACAATAAATCA

ATTTCGTTTCGTACCTTATGACGTTAAAGCATTCAAATGGTATAGGGCAC

TGGCG

SEQ ID NO:5 shows the nucleotide sequence of a T7 phage promoter.

SEQ ID NO:6 presents a YFP hairpin-RNA-forming sequence v2 as found in a plant expression vector. Upper case bases are YFP sense strand, underlined bases comprise an ST-LS 1 intron, lower case, and non-underlined bases are YFP antisense strand.

ATGTCATCTGGAGCACTTCTCTTTCATGGGAAGATTCCTTACGTTGTGGA

GATGGAAGGGAATGTTGATGGCCACACCTTTAGCATACGTGGGAAAGGCT

ACGGAGATGCCTCAGTGGGAAAGgactagtaccggttgggaaaggtatgt ttctgcttctacctttgatatatatataataattatcactaattagtagt aatatagtatttcaagtatttttttcaaaataaaagaatgtagtatatag ctattgcttttctgtagtttataagtgtgtatattttaatttataacttt tctaatatatgaccaaaacatggtgatgtgcaggttgatccgcggttact ttcccactgaggcatctccgtagcctttcccacgtatgctaaaggtgtgg ccatcaacattcccttccatctccacaacgtaaggaatcttcccatgaaa gagaagtgctccagatgacat SEQ ID NO:7 shows an exemplary DNA comprising an ST-LS1 intron.

SEQ ID NOs:8-11 show primers used for PCR amplification of a BSB_kr-1 and BSB_kr-2 polynucleotide.

SEQ ID NO:12 shows the DNA template for the sense strand of an exemplary YFP dsRNA (YFPv2):

```
CATCTGGAGCACTTCTCTTTCATGGGAAGATTCCTTACGTTGTGGAGATG

GAAGGGAATGTTGATGGCCACACCTTTAGCATACGTGGGAAAGGCTACGG

AGATGCCTCAGTGGGAAAGGTTGATGCACAGTTCATCTGCACAACTGGTG

ATGTTCCTGTGCCTTGGAGCACACTTGTCACCACTCTCACCTATGGAGCA

CAGTGCTTTGCCAAGTATGGTCCAGAGTTGAAGGACTTCTACAAGTCCTG

TATGCCAGATGGCTATGTGCAAGAGCGCACAATCACCTTTGAAGGAGATG

G
```

SEQ ID NOs:13 and 14 show primers used for PCR amplification of a YFP gene.

SEQ ID NOs:15-17 show exemplary RNAs transcribed from nucleic acids comprising exemplary kruppel polynucleotides and fragments thereof.

SEQ ID NO:18 shows Actin-ORF.

```
TACAAAATGTGTGACGAAGAAGTTGCTGCTTTAGTTGTAGACAATGGATC

TGGTATGTGCAAAGCCGGTTTCGCTGGAGATGATGCACCCCGAGCTGTAT

TCCCATCAATTGTTGGCAGGCCTAGACACCAGGGTGTCATGGTTGGAATG

GGACAAAAGGACAGTTATGTTGGAGACGAAGCCCAAAGCAAGAGAGGTAT

CCTCACCCTGAAATACCCCATTGAACACGGTATCATCACCAACTGGGACG

ACATGGAAAGATCTGGCATCACACCTTCTACAACGAGCTGCGAGTCGCT

CCAGAGGAACACCCCATCCTCCTGACTGAGGCTCCCCTCAACCCCAAAGC

CAACAGGGAGAAGATGACCCAGATCATGTTTGAGACCTTCAACACCCCAG

CCATGTATGTCGCCATCCAGGCTGTACTCTCCCTCTATGCCTCCGGTCGT

ACTACCGGTATTGTACTTGACTCAGGAGATGGTGTCTCCCACACCGTACC

CATCTATGAAGGTTATGCCCTTCCCCACGCCATCCTCCGTCTGGATCTTG

CTGGACGTGACTTGACTGACTATCTTATGAAGATCCTCACCGAGCGTGGT

TACAGCTTCACCACCACCGCTGAAAGGGAAATCGTCAGGGACATCAAGGA

AAAACTGTGCTATGTCGCCCTGGACTTTGAGCAGGAAATGGCCACCGCCG

CTGCCTCCACCTCCCTGGAGAAGTCCTATGAACTTCCCGACGGTCAGGTC

ATCACCATCGGTAACGAGAGGTTCCGTTGCCCAGAGGCTCTCTTCCAGCC

TTCCTTCTTGGGTATGGAATCTTGCGGTATCCATGAGACTGTCTACAACT

CCATCATGAAGTGCGACGTTGACATCAGGAAGGACTTGTACGCCAACACC

GTCCTCTCCGGAGGTACCACCATGTACCCAGGTATTGCTGACAGGATGCA

GAAGGAAATCACCGCCCTCGCTCCTTCAACCATCAAGATCAAGATCATTG

CTCCCCCAGAAAGGAAGTACTCCGTATGGATCGGTGGTTCCATCTTGGCT

TCCCTGTCCACCTTCCAGCAGATGTGGATCTCCAAGCAGGAATACGACGA

ATCCGGCCCAGGCATCGTCCACCGCAAATGCTTC
```

SEQ ID NOs:19-21 show primers and probes used for actin qPCR.

DETAILED DESCRIPTION

I. Overview of Several Embodiments

We developed RNA interference (RNAi) as a tool for insect pest management, using a target pest species for transgenic plants that express dsRNA; the Neotropical brown stink bug. Thus far, most genes proposed as targets for RNAi in particular insects do not achieve their purpose, and those useful targets that have been identified involve typically those that cause lethality in the nymph stage. Herein, we describe RNAi-mediated knockdown of kruppel (kr) in the Neotropical brown stink bug, which is shown to disrupt embryonic development when, for example, iRNA molecules are delivered via kruppel dsRNA provided to adult females. However, there was almost complete absence of hatching in the eggs collected from females exposed to kruppel dsRNA. In embodiments herein, the ability to deliver kruppel dsRNA by injection to adult insects confers a pRNAi effect that is very useful for insect (e.g., hemipteran) pest management. Furthermore, the potential to affect multiple target sequences in both nymph and adult hemipteran pests may increase opportunities to develop sustainable approaches to insect pest management involving RNAi technologies.

Disclosed herein are methods and compositions for genetic control of hemipteran pest infestations. Methods for identifying one or more gene(s) essential to the lifecycle of a hemipteran pest (e.g., gene(s) essential for normal reproductive capacity and/or embryonic and/or nymph development) for use as a target gene for RNAi-mediated control of a hemipteran pest population are also provided. DNA plasmid vectors encoding an RNA molecule may be designed to suppress one or more target gene(s) essential for growth, survival, development, and/or reproduction. In some embodiments, the RNA molecule may be capable of forming dsRNA molecules. In some embodiments, methods are provided for post-transcriptional repression of expression or inhibition of a target gene via nucleic acid molecules that are complementary to a coding or non-coding sequence of the target gene in a hemipteran pest. In these and further embodiments, a hemipteran pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Other embodiments involve sequence-specific inhibition of expression of target gene products, using dsRNA, siRNA, shRNA, miRNA and/or hpRNA that is complementary to coding and/or non-coding sequences of the target gene(s) to achieve at least partial control of a hemipteran pest. Disclosed is a set of isolated and purified nucleic acid molecules comprising a polynucleotide, for example, as set forth in SEQ ID NO:1, and fragments thereof. In some embodiments, a stabilized dsRNA molecule may be expressed from these polynucleotides, fragments thereof, or a gene comprising one of these polynucleotides, for the post-transcriptional silencing or inhibition of a target gene. In certain embodiments, isolated and purified nucleic acid molecules comprise all or part of any of SEQ ID NOs:1, 3, and 4.

Some embodiments involve a recombinant host cell (e.g., a plant cell) having in its genome at least one recombinant DNA encoding at least one iRNA (e.g., dsRNA) molecule(s). In particular embodiments, the dsRNA molecule(s) may be produced when ingested by a hemipteran pest to post-transcriptionally silence or inhibit the expression of a target gene in the pest or progeny of the pest. The recombinant DNA may comprise, for example, SEQ ID NO:1, fragments of SEQ ID NO:1, and a polynucleotide consisting of a partial sequence of a gene comprising SEQ ID NO:1, and/or complements thereof.

Alternative embodiments involve a recombinant host cell having in its genome a recombinant DNA encoding at least one iRNA (e.g., dsRNA) molecule(s) comprising all or part of SEQ ID NO:15 (e.g., SEQ ID NOs:15-17). When ingested by a hemipteran pest, the iRNA molecule(s) may silence or inhibit the expression of a target kruppel gene (e.g., a DNA comprising all or part of the polynucleotide of SEQ ID NO:1) in the pest or progeny of the pest, and thereby result in cessation of reproduction in the pest, and/or growth, development, and/or feeding in progeny of the pest.

In some embodiments, a recombinant host cell having in its genome at least one recombinant DNA encoding at least one RNA molecule capable of forming a dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA(s). In particular embodiments, an RNA molecule capable of forming a dsRNA molecule may be expressed in a transgenic plant cell. Therefore, in these and other embodiments, a dsRNA molecule may be isolated from a transgenic plant cell. In particular embodiments, the transgenic plant is a plant selected from the group comprising corn (*Zea mays*), soybean (*Glycine max*), cotton (*Gossypium* spp.), and plants of the family Poaceae.

Other embodiments involve a method for modulating the expression of a target gene in a hemipteran pest cell. In these and other embodiments, a nucleic acid molecule may be provided, wherein the nucleic acid molecule comprises a polynucleotide encoding an RNA molecule capable of forming a dsRNA molecule. In particular embodiments, a polynucleotide encoding an RNA molecule capable of forming a dsRNA molecule may be operatively linked to a promoter, and may also be operatively linked to a transcription termination sequence. In particular embodiments, a method for modulating the expression of a target gene in a hemipteran pest cell may comprise: (a) transforming a plant cell with a vector comprising a polynucleotide encoding an RNA molecule capable of forming a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the RNA molecule capable of forming a dsRNA molecule encoded by the polynucleotide of the vector. A plant may be regenerated from a plant cell that has the vector integrated in its genome and comprises the dsRNA molecule encoded by the polynucleotide of the vector.

Thus, also disclosed is a transgenic plant comprising a vector having a polynucleotide encoding an RNA molecule capable of forming a dsRNA molecule integrated in its genome, wherein the transgenic plant comprises the dsRNA molecule encoded by the polynucleotide of the vector. In particular embodiments, expression of an RNA molecule capable of forming a dsRNA molecule in the plant is sufficient to modulate the expression of a target gene in a cell of a hemipteran pest that contacts the transformed plant or plant cell (for example, by feeding on the transformed plant, a part of the plant (e.g., leaves or plant cell) or in a cell of a progeny of the hemipteran pest that contacts the transformed plant or plant cell (for example, by parental transmission), such that reproduction of the pest is inhibited. Transgenic plants disclosed herein may display tolerance and/or protection from hemipteran pest infestations. Particular transgenic plants may display protection and/or enhanced protection from one or more pest(s) selected from the group consisting of: *Piezodorus guildinii*; *Halyomorpha halys*; *Nezara viridula*; *Acrosternum hilare*; *Euschistus heros*; *Euschistus serous*, *Chinavia hilare*; *C. marginatum*; *Dichelops melacanthus*; *D. furcatus*; *Edessa meditabunda*; *Thyanta perditor*; *Horcias nobilellus*; *Taedia stigmosa*; *Dysdercus peruvianus*; *Neomegalotomus parvus*; *Leptoglossus zonatus*; *Niesthrea sidae*; *Lygus hesperus*; and *L. lineolaris*.

Also disclosed herein are methods for delivery of control agents, such as an iRNA molecule, to a hemipteran pest. Such control agents may cause, directly or indirectly, an impairment in the ability of a hemipteran pest population to feed, grow or otherwise cause damage in a host. In some embodiments, a method is provided comprising delivery of a stabilized dsRNA molecule to a hemipteran pest to suppress at least one target gene in the pest or its progeny, thereby causing parental RNAi and reducing or eliminating plant damage in a pest host. In some embodiments, a method of inhibiting expression of a target gene in a hemipteran pest may result in cessation of reproduction in the pest, and/or growth, development, and/or feeding in progeny of the pest. In some embodiments, the method may significantly reduce the size of a subsequent pest generation in an infestation, without directly resulting in mortality in the pest(s) that contact the iRNA molecule. In some embodiments, the method may significantly reduce the size of a subsequent pest generation in an infestation, while also resulting in mortality in the pest(s) that contact the iRNA molecule.

In some embodiments, compositions (e.g., a topical composition) are provided that comprise an iRNA (e.g., dsRNA) molecule for use with plants, animals, and/or the environment of a plant or animal to achieve the elimination or reduction of a hemipteran pest infestation. In particular embodiments, the composition may be a nutritional composition or resource, or food source to be fed to the hemipteran pest. Some embodiments comprise making the nutritional composition or food source available to the pest. Ingestion of a composition comprising iRNA molecules may result in the uptake of the molecules by one or more cells of the hemipteran pest, which may in turn result in the inhibition of expression of at least one target gene in cell(s) of the pest or its progeny. Ingestion of or damage to a plant or plant cell by a hemipteran pest infestation may be limited or eliminated in or on any host tissue or environment in which the pest is present by providing one or more compositions comprising an iRNA molecule in the host of the pest.

The compositions and methods disclosed herein may be used together in combinations with other methods and compositions for controlling damage by hemipteran pests. For example, an iRNA molecule as described herein for protecting plants from hemipteran pests may be used in a method comprising the additional use of one or more chemical agents effective against a hemipteran pest, biopesticides effective against a hemipteran pest, crop rotation, recombinant genetic techniques that exhibit features different from the features of RNAi-mediated methods and RNAi compositions (e.g., recombinant production of proteins in plants that are harmful to a hemipteran pest (e.g., Bt toxins)), and/or recombinant expression of non-parental iRNA molecules (e.g., lethal iRNA molecules that result in the cessation of growth, development, feeding and/or cause mortality in the hemipteran pest that ingests the iRNA molecule).

II. Abbreviations

BSB Neotropical brown stink bug (*Euschistus heros*)
dsRNA double-stranded ribonucleic acid
GI growth inhibition NCBI National Center for Biotechnology Information
gDNA genomic Deoxyribonucleic Acid
iRNA inhibitory ribonucleic acid
ORF open reading frame
RNAi ribonucleic acid interference
miRNA micro ribonucleic acid
siRNA small inhibitory ribonucleic acid
hpRNA hairpin ribonucleic acid
shRNA short hairpin ribonucleic acid
pRNAi parental RNA interference
UTR untranslated region
PCR Polymerase chain reaction
qPCR quantative polymerase chain reaction
RISC RNA-induced Silencing Complex
RH relative humidity
SEM standard error of the mean
YFP yellow fluorescent protein III. Terms In the description and tables which follow, a number of terms are used. In order to provide a clear and consistent understanding of the specification and claims, including the scope to be given such terms, the following definitions are provided:

Contact (with an organism): As used herein, the term "contact with" or "uptake by" an organism (e.g., a hemipteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; injection of the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, Zea mays (maize).

Expression: As used herein, "expression" of a coding polynucleotide (for example, a gene or a transgene) refers to the process by which the coded information of a nucleic acid transcriptional unit (including, e.g., gDNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Genetic material: As used herein, the term "genetic material" includes all genes, and nucleic acid molecules, such as DNA and RNA.

Hemipteran pest: As used herein, the term "hemipteran pest" refers to pest insects of the order Hemiptera, including, for example and without limitation, insects in the families Pentatomidae, Miridae, Pyrrhocoridae, Coreidae, Alydidae, and Rhopalidae, which feed on a wide range of host plants and have piercing and sucking mouth parts. In particular examples, a hemipteran pest is selected from the list comprising *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus serous* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

Inhibition: As used herein, the term "inhibition," when used to describe an effect on a coding polynucleotide (for example, a gene), refers to a measurable decrease in the cellular level of mRNA transcribed from the coding polynucleotide and/or peptide, polypeptide, or protein product of the coding polynucleotide. In some examples, expression of a coding polynucleotide may be inhibited such that expression is approximately eliminated. "Specific inhibition" refers to the inhibition of a target coding polynucleotide without consequently affecting expression of other coding polynucleotides (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, gDNA, and synthetic forms and mixed polymers of the above. A nucleotide or nucleobase may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleic acid molecule refers to a polynucleotide having nucleobases that may form base pairs with the nucleobases of the nucleic acid molecule (i.e., A-T/U, and G-C).

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule.

Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

```
ATGATGATG   polynucleotide
TACTACTAC   "complement" of the polynucleotide
CATCATCAT   "reverse complement" of the
            polynucleotide
```

Some embodiments of the invention may include hairpin RNA-forming RNAi molecules. In these RNAi molecules, both the complement of a nucleic acid to be targeted by RNA interference and the reverse complement may be found in the same molecule, such that the single-stranded RNA molecule may "fold over" and hybridize to itself over region comprising the complementary and reverse complementary polynucleotides.

"Nucleic acid molecules" include all polynucleotides, for example: single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), shRNA (small hairpin RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, gDNA, and DNA-RNA hybrids. The terms "polynucleotide" and "nucleic acid," and "fragments" thereof will be understood by those in the art as a term that includes both gDNAs, ribosomal RNAs, transfer RNAs, messenger RNAs, operons, and smaller engineered polynucleotides that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleic acid, they may be used as probes for detecting DNA or RNA. Oligonucleotides composed of DNA (oligodeoxyribonucleotides) may be used in PCR, a technique for the amplification of DNAs. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding polynucleotide," "structural polynucleotide," or "structural nucleic acid molecule" refers to a polynucleotide that is ultimately translated into a polypeptide, via transcription and mRNA, when placed under the control of appropriate regulatory elements. With respect to RNA, the term "coding polynucleotide" refers to a polynucleotide that is translated into a peptide, polypeptide, or protein. The boundaries of a coding polynucleotide are determined by a translation start codon at the 5'-terminus and a translation stop codon at the 3'-terminus. Coding polynucleotides include, but are not limited to: gDNA; cDNA; EST; and recombinant polynucleotides.

As used herein, "transcribed non-coding polynucleotide" refers to segments of mRNA molecules such as 5'UTR, 3'UTR and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18S rRNA, 23S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "spacer" in a nucleic acid and which is transcribed into an RNA molecule.

Lethal RNA interference: As used herein, the term "lethal RNA interference" refers to RNA interference that results in death or a reduction in viability of the subject individual to which, for example, a dsRNA, miRNA, siRNA, shRNA, and/or hpRNA is delivered.

Parental RNA interference: As used herein, the term "parental RNA interference" (pRNAi) refers to a RNA interference phenotype that is observable in progeny of the subject (e.g., a hemipteran pest) to which, for example, a dsRNA, miRNA, siRNA, shRNA, and/or hpRNA is delivered. In some embodiments, pRNAi comprises the delivery of a dsRNA to a hemipteran pest, wherein the pest is thereby rendered less able to produce viable offspring. A nucleic acid that initiates pRNAi may or may not increase the incidence of mortality in a population into which the nucleic acid is delivered. In certain examples, the nucleic acid that initiates pRNAi does not increase the incidence of mortality in the population into which the nucleic acid is delivered. For example, a population of hemipteran pests may be fed one or more nucleic acids that initiate pRNAi, wherein the pests survive and mate but produce eggs that are less able to hatch viable progeny than eggs produced by pests of the same species that are not fed the nucleic acid(s). In one mechanism of pRNAi, parental RNAi delivered to a female is able to knockdown zygotic gene expression in offspring embryos of the female. Bucher et al. (2002) Curr. Biol. 12(3):R85-6.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell, such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome," as it applies to bacteria, refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two polynucleotides or polypeptides, refers to the residues in the sequences of the two molecules that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) of a molecule over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acids with even greater sequence similarity to the sequences of the reference polynucleotides will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleobases of the two nucleic acid molecules. The two molecules are then able to form hydrogen bonds with corresponding bases on the opposite strand to form a duplex molecule that, if it is sufficiently stable, is detectable using methods well known in the art. A polynucleotide need not be 100% complementary to its target nucleic acid to be specifically hybridizable. However, the amount of complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acids. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N Y, 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N Y, 1993; and Ausubel et al., Eds., *Current Protocols in Molecular Biology*, Chapter 2, Greene Publishing and Wiley-Interscience, N Y, 1995.

As used herein, "stringent conditions" encompass conditions under which hybridization will only occur if there is less than 20% mismatch between the sequence of the hybridization molecule and a homologous polynucleotide within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions. High Stringency condition (detects polynucleotides that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects polynucleotides that share at least 80% sequence identity): Hybridization in 5x-6xSSC buffer at 65-70° C. for 16-20 hours; wash twice in 2xSSC buffer at room temperature for 5-20 minutes each; and wash twice in 1xSSC buffer at 55-70° C. for 30 minutes each.

Non-stringent control condition (polynucleotides that share at least 50% sequence identity will hybridize): Hybridization in 6xSSC buffer at room temperature to 55° C. for 16-20 hours; wash at least twice in 2x-3xSSC buffer at room temperature to 55° C. for 20-30 minutes each.

As used herein, the term "substantially homologous" or "substantial homology," with regard to a nucleic acid, refers to a polynucleotide having contiguous nucleobases that hybridize under stringent conditions to the reference nucleic acid. For example, nucleic acids that are substantially homologous to a reference nucleic acid of any of SEQ ID NOs:1, 3, and 4 are those nucleic acids that hybridize under stringent conditions (e.g., the Moderate Stringency conditions set forth, supra) to the reference nucleic acid of any of SEQ ID NOs:1, 3, and 4. Substantially homologous polynucleotides may have at least 80% sequence identity. For example, substantially homologous polynucleotides may have from about 80% to 100% sequence identity, such as 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target polynucleotides under conditions where specific binding is desired, for example, under stringent hybridization conditions.

As used herein, the term "ortholog" refers to a gene in two or more species that has evolved from a common ancestral nucleic acid, and may retain the same function in the two or more species.

As used herein, two nucleic acid molecules are said to exhibit "complete complementarity" when every nucleotide of a polynucleotide read in the 5' to 3' direction is complementary to every nucleotide of the other polynucleotide when read in the 3' to 5' direction. A polynucleotide that is complementary to a reference polynucleotide will exhibit a sequence identical to the reverse complement of the reference polynucleotide. These terms and descriptions are well defined in the art and are easily understood by those of ordinary skill in the art.

Operably linked: A first polynucleotide is operably linked with a second polynucleotide when the first polynucleotide is in a functional relationship with the second polynucleotide. When recombinantly produced, operably linked polynucleotides are generally contiguous, and, where necessary to join two protein-coding regions, in the same reading frame (e.g., in a translationally fused ORF). However, nucleic acids need not be contiguous to be operably linked.

The term, "operably linked," when used in reference to a regulatory genetic element and a coding polynucleotide, means that the regulatory element affects the expression of the linked coding polynucleotide. "Regulatory elements," or "control elements," refer to polynucleotides that influence the timing and level/amount of transcription, RNA processing or stability, or translation of the associated coding polynucleotide. Regulatory elements may include promoters; translation leaders; introns; enhancers; stem-loop structures; repressor binding polynucleotides; polynucleotides with a termination sequence; polynucleotides with a polyadenylation recognition sequence; etc. Particular regulatory elements may be located upstream and/or downstream of a coding polynucleotide operably linked thereto. Also, particular regulatory elements operably linked to a coding polynucleotide may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding polynucleotide for expression in a cell, or a promoter may be operably linked to a polynucleotide encoding a signal peptide which may be operably linked to a coding polynucleotide for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, XbaI/NcoI fragment 5' to the *Brassica napus* ALS3 structural gene (or a polynucleotide similar to said XbaI/NcoI fragment) (International PCT Publication No. WO96/30530).

Additionally, any tissue-specific or tissue-preferred promoter may be utilized in some embodiments of the invention. Plants transformed with a nucleic acid molecule comprising a coding polynucleotide operably linked to a tissue-specific promoter may produce the product of the coding polynucleotide exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco;

an anther-specific promoter such as that from LAT52; a pollen-specific promoter such as that from Zm13; and a microspore-preferred promoter such as that from apg.

Soybean plant: As used herein, the term "soybean plant" refers to a plant of the species *Glycine* sp.; for example, *G. max*.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Felgner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid. In some examples, a transgene may be a DNA that encodes one or both strand(s) of a RNA capable of forming a dsRNA molecule that comprises a polynucleotide that is complementary to a nucleic acid molecule found in a hemipteran pest. In further examples, a transgene may be an antisense polynucleotide, wherein expression of the antisense polynucleotide inhibits expression of a target nucleic acid, thereby producing a parental RNAi phenotype. In still further examples, a transgene may be a gene (e.g., a herbicide-tolerance gene, a gene encoding an industrially or pharmaceutically useful compound, or a gene encoding a desirable agricultural trait). In these and other examples, a transgene may contain regulatory elements operably linked to a coding polynucleotide of the transgene (e.g., a promoter).

Vector: A nucleic acid molecule as introduced into a cell, for example, to produce a transformed cell. A vector may include genetic elements that permit it to replicate in the host cell, such as an origin of replication. Examples of vectors include, but are not limited to: a plasmid; cosmid; bacteriophage; or virus that carries exogenous DNA into a cell. A vector may also include one or more genes, including ones that produce antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% or greater relative to the yield of check varieties in the same growing location containing significant densities of the hemipteran pests that are injurious to that crop growing at the same time and under the same conditions, which are targeted by the compositions and methods herein.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Hemipteran Pest Polynucleotide

A. Overview

Described herein are nucleic acid molecules useful for the control of hemipteran pests. Described nucleic acid molecules include target polynucleotides (e.g., native genes, and non-coding polynucleotides), dsRNAs, siRNAs, shRNAs, hpRNAs, and miRNAs. For example, dsRNA, siRNA, miRNA, shRNA, and/or hpRNA molecules are described in some embodiments that may be specifically complementary to all or part of one or more native nucleic acids in a hemipteran pest. In these and further embodiments, the native nucleic acid(s) may be one or more target gene(s), the product of which may be, for example and without limitation: involved in a reproductive process or involved in nymph development. Nucleic acid molecules described herein, when introduced into a cell (e.g., through parental transmission) comprising at least one native nucleic acid(s) to which the nucleic acid molecules are specifically complementary, may initiate RNAi in the cell, and consequently reduce or eliminate expression of the native nucleic acid(s). In some examples, reduction or elimination of the expression of a target gene by a nucleic acid molecule specifically complementary thereto may result in reduction or cessation of reproduction in the hemipteran pest, and/or growth, development, and/or feeding in progeny of the pest. These methods may significantly reduce the size of a subsequent pest generation in an infestation, for example, without directly resulting in mortality in the pest(s) that contact the iRNA molecule.

In some embodiments, at least one target gene in a hemipteran pest may be selected, wherein the target gene comprises a kruppel polynucleotide. In particular examples, a target gene in a hemipteran pest is selected, wherein the target gene comprises a polynucleotide selected from among any of SEQ ID NOs:1, 3, and 4.

In other embodiments, a target gene may be a nucleic acid molecule comprising a polynucleotide that can be reverse translated in silico to a polypeptide comprising a contiguous amino acid sequence that is at least about 85% identical (e.g., at least 84%, 85%, about 90%, about 95%, about 96%, about 97%, about 98%, about 99%, about 100%, or 100% identical) to the amino acid sequence of a protein product of a kruppel polynucleotide (i.e., a KRUPPEL polypeptide). A target gene may be any nucleic acid in a hemipteran pest, the post-transcriptional inhibition of which has a deleterious effect on the capacity of the pest to produce viable offspring, for example, to provide a protective benefit against the pest to a plant. In particular examples, a target gene is a nucleic acid molecule comprising a polynucleotide that can be reverse translated in silico to a polypeptide comprising a contiguous amino acid sequence that is at least about 85% identical, about 90% identical, about 95% identical, about 96% identical, about 97% identical, about 98% identical, about 99% identical, about 100% identical, or 100% identical to the amino acid sequence that is the in silico translation product of SEQ ID NO:2.

Provided in some embodiments are DNAs, the expression of which results in an RNA molecule comprising a polynucleotide that is specifically complementary to all or part of a native RNA molecule that is encoded by a coding polynucleotide in a hemipteran pest. In some embodiments, after ingestion of the expressed RNA molecule by a hemipteran pest, down-regulation of the coding polynucleotide in cells of the pest, or in cells of progeny of the pest, may be obtained. In particular embodiments, down-regulation of the coding polynucleotide in cells of the hemipteran pest may result in reduction or cessation of reproduction and/or proliferation in the pest, and/or growth, development, and/or feeding in progeny of the pest.

In some embodiments, target polynucleotides include transcribed non-coding RNAs, such as 5'UTRs; 3'UTRs; spliced leaders; introns; outrons (e.g., 5'UTR RNA subsequently modified in trans splicing); donatrons (e.g., non-coding RNA required to provide donor sequences for trans splicing); and other non-coding transcribed RNA of target hemipteran pest genes. Such polynucleotides may be derived from both mono-cistronic and poly-cistronic genes.

Thus, also described herein in connection with some embodiments are iRNA molecules (e.g., dsRNAs, siRNAs, miRNAs, shRNAs, and hpRNAs) that comprise at least one polynucleotide that is specifically complementary to all or part of a target nucleic acid in a hemipteran pest. In some embodiments an iRNA molecule may comprise polynucleotide(s) that are complementary to all or part of a plurality of target nucleic acids; for example, 2, 3, 4, 5, 6, 7, 8, 9, 10, or more target nucleic acids. In particular embodiments, an iRNA molecule may be produced in vitro, or in vivo by a genetically-modified organism, such as a plant or bacterium. Also disclosed are cDNAs that may be used for the production of dsRNA molecules, siRNA molecules, miRNA molecules, shRNA molecules, and/or hpRNA molecules that are specifically complementary to all or part of a target nucleic acid in a hemipteran pest. Further described are recombinant DNA constructs for use in achieving stable transformation of particular host targets. Transformed host targets may express effective levels of dsRNA, siRNA, miRNA, shRNA, and/or hpRNA molecules from the recombinant DNA constructs. Also described is a plant transformation vector comprising at least one polynucleotide operably linked to a heterologous promoter functional in a plant cell, wherein expression of the polynucleotide(s) results in an RNA molecule comprising a string of contiguous nucleobases that is specifically complementary to all or part of a target nucleic acid in a hemipteran pest.

In particular embodiments, nucleic acid molecules useful for the control of hemipteran pests may include: all or part of a native nucleic acid isolated from *Euschistus* comprising a kruppel polynucleotide (e.g., SEQ ID NO:1); DNAs that when expressed result in an RNA molecule comprising a polynucleotide that is specifically complementary to all or part of a native RNA molecule that is encoded by kruppel; iRNA molecules (e.g., dsRNAs, siRNAs, miRNAs, shRNAs, and hpRNAs) that comprise at least one polynucleotide that is specifically complementary to all or part of a RNA molecule encoded by kruppel; cDNAs that may be used for the production of dsRNA molecules, siRNA molecules, miRNA molecules, shRNA molecules, and/or hpRNA molecules that are specifically complementary to all or part of an RNA molecule encoded by kruppel; and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA, shRNA, and hpRNA) molecules that inhibit target gene expression in a cell, tissue, or organ of a hemipteran pest; and DNA molecules capable of being expressed as an iRNA molecule in a cell or microorganism to inhibit target gene expression in a cell, tissue, or organ of a hemipteran pest.

Some embodiments of the invention provide an isolated nucleic acid molecule comprising at least one (e.g., one, two, three, or more) polynucleotide(s) selected from the group consisting of: SEQ ID NO:1; the complement of SEQ ID NO:1; a fragment of at least 15 contiguous nucleotides (e.g., at least 19 contiguous nucleotides) of SEQ ID NO:1 (e.g., SEQ ID NO:3 and SEQ ID NO:4); the complement of a fragment of at least 15 contiguous nucleotides of SEQ ID NO:1; a native coding polynucleotide of a hemipteran organism (e.g., BSB) comprising SEQ ID NO:1; the complement of a native coding polynucleotide of a hemipteran organism comprising SEQ ID NO:1; a fragment of at least 15 contiguous nucleotides of a native coding polynucleotide of a hemipteran organism comprising SEQ ID NO:1; and the complement of a fragment of at least 15 contiguous nucleotides of a native coding polynucleotide of a hemipteran organism comprising SEQ ID NO:1. In particular embodiments, contact with or uptake by a hemipteran pest of the isolated polynucleotide inhibits the growth, development, reproduction and/or feeding of the pest.

In other embodiments, an isolated nucleic acid molecule of the invention may comprise at least one (e.g., one, two, three, or more) polynucleotide(s) selected from the group consisting of: SEQ ID NO:15; the complement of SEQ ID NO:15; SEQ ID NO:16; the complement of SEQ ID NO:16; SEQ ID NO:17; the complement of SEQ ID NO:17; a fragment of at least 15 contiguous nucleotides of any of SEQ ID NOs:15-17; the complement of a fragment of at least 15 contiguous nucleotides of any of SEQ ID NOs:15-17; a native polyribonucleotide transcribed in a hemipteran organism from a gene comprising SEQ ID NO:1; the complement of a native polyribonucleotide transcribed in a hemipteran organism from a gene comprising SEQ ID NO:1; a fragment of at least 15 contiguous nucleotides of a native polyribonucleotide transcribed in a hemipteran organism from a gene comprising SEQ ID NO:1; and the complement of a fragment of at least 15 contiguous nucleotides of a native polyribonucleotide transcribed in a hemipteran organism from a gene comprising SEQ ID NO:1. In particular embodiments, contact with or uptake by a hemipteran pest of the isolated polynucleotide inhibits the growth, development, reproduction and/or feeding of the pest.

In alternative embodiments, a nucleic acid molecule of the invention may comprise at least one (e.g., one, two, three, or more) DNA(s) capable of being expressed as an iRNA molecule in a cell or microorganism to inhibit target gene expression in a cell, tissue, or organ of a hemipteran pest. Such DNA(s) may be operably linked to a promoter that functions in a cell comprising the DNA molecule to initiate or enhance the transcription of the encoded RNA capable of forming a dsRNA molecule(s). In one embodiment, the at least one (e.g., one, two, three, or more) DNA(s) may be derived from the polynucleotide of SEQ ID NO:1. Derivatives of SEQ ID NO:1 include fragments of SEQ ID NO:1. In some embodiments, such a fragment may comprise, for example, at least about 15 contiguous nucleotides of SEQ ID NO:1 or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NO:1 or a complement thereof. In some examples, such a fragment may comprise, for example, at least 19 contiguous nucleotides (e.g., 19, 20, 21, 22, 23, 24, 25, 26, 27, 28, 29, or 30 contiguous nucleotides) of SEQ ID NO:1 or a complement thereof.

Some embodiments comprise introducing partially- or fully-stabilized dsRNA molecules into a hemipteran pest to inhibit expression of a target gene in a cell, tissue, or organ of the hemipteran pest. When expressed as an iRNA molecule (e.g., dsRNA, siRNA, miRNA, shRNA, and hpRNA) and taken up by a hemipteran pest, polynucleotides comprising one or more fragments of SEQ ID NO:1 (e.g., SEQ ID NO:3 and SEQ ID NO:4), and the complements thereof, may cause one or more of death, developmental arrest, growth inhibition, change in sex ratio, reduction in brood size, cessation of infection, and/or cessation of feeding by a hemipteran pest. In particular examples, polynucleotides comprising one or more fragments (e.g., polynucleotides including about 15 to about 300 nucleotides) of SEQ ID NO:1, and the complements thereof cause a reduction in the capacity of an existing generation of the pest to produce a subsequent generation of the pest.

In certain embodiments, dsRNA molecules provided by the invention comprise polynucleotides complementary to a transcript from a target gene comprising SEQ ID NO:1, and/or polynucleotides complementary to a fragment of SEQ ID NO:1, the inhibition of which target gene in a hemipteran pest results in the reduction or removal of a polypeptide or polynucleotide agent that is essential for the pest's or the pest's progeny's growth, development, or other biological function. A selected polynucleotide may exhibit from about 80% to about 100% sequence identity to SEQ ID NO:1, a contiguous fragment of SEQ ID NO:1, or the complement of either of the foregoing. For example, a selected polynucleotide may exhibit 79%; 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; about 98.5%; about 99%; about 99.5%; or about 100% sequence identity to SEQ ID NO:1, a contiguous fragment of SEQ ID NO:1, or the complement of either of the foregoing.

In some embodiments, a DNA molecule capable of being expressed as an iRNA molecule in a cell or microorganism to inhibit target gene expression may comprise a single polynucleotide that is specifically complementary to all or part of a native polynucleotide found in one or more target hemipteran pest species, or the DNA molecule can be constructed as a chimera from a plurality of such specifically complementary polynucleotides.

In other embodiments, a nucleic acid molecule may comprise a first and a second polynucleotide separated by a "linker." A linker may be a region comprising any sequence of nucleotides that facilitates secondary structure formation between the first and second polynucleotides, where this is desired. In one embodiment, the linker is part of a sense or antisense coding polynucleotide for mRNA. The linker may alternatively comprise any combination of nucleotides or homologues thereof that are capable of being linked covalently to a nucleic acid molecule. In some examples, the linker may comprise an intron (e.g., as ST-LS1 intron).

For example, in some embodiments, the DNA molecule may comprise a polynucleotide coding for one or more different RNA molecules, wherein each of the different RNA molecules comprises a first polynucleotide and a second polynucleotide, wherein the first and second polynucleotides are complementary to each other. The first and second polynucleotides may be connected within an RNA molecule by a spacer. The spacer may constitute part of the first polynucleotide or the second polynucleotide. Expression of an RNA molecule comprising the first and second nucleotide polynucleotides may lead to the formation of a dsRNA molecule of the present invention, by specific intramolecular base-pairing of the first and second nucleotide polynucleotides. The first polynucleotide or the second polynucleotide may be substantially identical to a polynucleotide native to a hemipteran pest (e.g., a target gene, or transcribed non-coding polynucleotide), a derivative thereof, or a complementary polynucleotide thereto.

dsRNA nucleic acid molecules comprise double strands of polymerized ribonucleotides, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNAs transcribed from a target gene, and both RNA molecules are subsequently degraded by an inherent cellular RNA-degrading mechanism. This process may result in the effective degradation or removal of the RNA encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in hemipteran pests.

In some embodiments, a nucleic acid molecule of the invention may include at least one non-naturally occurring polynucleotide that can be transcribed into a single-stranded RNA molecule capable of forming a dsRNA molecule in vivo through intermolecular hybridization. Such dsRNAs typically self-assemble, and can be provided in the nutrition source of a hemipteran pest to achieve the post-transcriptional inhibition of a target gene. In these and further embodiments, a nucleic acid molecule of the invention may comprise two different non-naturally occurring polynucleotides, each of which is specifically complementary to a different target gene in a hemipteran pest. When such a nucleic acid molecule is provided as a dsRNA molecule to a hemipteran pest, the dsRNA molecule inhibits the expression of at least two different target genes in the pest.

C. Obtaining Nucleic Acid Molecules

A variety of polynucleotides in hemipteran pests may be used as targets for the design of nucleic acid molecules of the invention, such as iRNAs and DNA molecules encoding iRNAs. Selection of native polynucleotides is not, however, a straight-forward process. Only a small number of native polynucleotides in the hemipteran pest will be effective targets. For example, it cannot be predicted with certainty whether a particular native polynucleotide can be effectively down-regulated by nucleic acid molecules of the invention, or whether down-regulation of a particular native polynucleotide will have a detrimental effect on the growth, viability, proliferation, and/or reproduction of the hemipteran pest. The vast majority of native hemipteran pest polynucleotides, such as ESTs isolated therefrom do not have a detrimental effect on the growth, viability, proliferation, and/or reproduction of the pest. Neither is it predictable which of the native polynucleotides that may have a detrimental effect on a hemipteran pest are able to be used in recombinant techniques for expressing nucleic acid molecules complementary to such native polynucleotides in a host plant and providing the detrimental effect on the pest upon feeding without causing harm to the host plant.

In some embodiments, nucleic acid molecules of the invention (e.g., dsRNA molecules to be provided in the host plant of a hemipteran pest) are selected to target cDNAs that encode proteins or parts of proteins essential for hemipteran pest reproduction and/or development, such as polypeptides involved in metabolic or catabolic biochemical pathways, cell division, reproduction, energy metabolism, embryonic development, nymph development, transcriptional regulation, and the like. As described herein, contact with compositions by a target organism containing one or more dsRNAs (e.g., by injection or topical contact), at least one segment of which is specifically complementary to at least a substantially identical segment of RNA produced in the cells of the target pest organism, can result in failure or reduction of the capacity to mate, oviposit eggs, or produce viable progeny. A polynucleotide, either DNA or RNA, derived from a hemipteran pest can be used to construct plant cells resistant to infestation by the pests. The host plant of the hemipteran pest (e.g., *Z. mays, G. max*, and *Gossypium* sp.), for example, can be transformed to contain one or more of the polynucleotides derived from the hemipteran pest as provided herein. The polynucleotide transformed into the host may encode one or more RNAs that form into a dsRNA structure in the cells or biological fluids within the transformed host, thus making the dsRNA available if/when the pest forms a nutritional relationship with the transgenic host. This may result in the suppression of expression of one or more genes in the cells of the pest, and ultimately inhibition of reproduction and/or development.

In alternative embodiments, a gene is targeted that is essentially involved in the growth, development and reproduction of a hemipteran pest. Other target genes for use in the present invention may include, for example, those that play important roles in hemipteran pest viability, movement, migration, growth, development, infectivity, and establishment of feeding sites. A target gene may therefore be a housekeeping gene or a transcription factor. Additionally, a native hemipteran pest polynucleotide for use in the present invention may also be derived from a homolog (e.g., an ortholog), of a plant, viral, bacterial or insect gene, the function of which is known to those of skill in the art, and the polynucleotide of which is specifically hybridizable with a target gene in the genome of the target hemipteran pest. Methods of identifying a homolog of a gene with a known nucleotide sequence by hybridization are known to those of skill in the art.

In some embodiments, the invention provides methods for obtaining a nucleic acid molecule comprising a polynucleotide for producing an iRNA (e.g., dsRNA, siRNA, miRNA, shRNA, and hpRNA) molecule. One such embodiment comprises: (a) analyzing one or more target gene(s) for their expression, function, and phenotype upon dsRNA-mediated gene suppression in a hemipteran pest; (b) probing a cDNA or gDNA library with a probe comprising all or a portion of a polynucleotide or a homolog thereof from a targeted hemipteran pest that displays an altered (e.g., reduced) reproduction or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA or a homolog thereof; and (f) chemically synthesizing all or a substantial portion of a gene, or an siRNA, miRNA, hpRNA, mRNA, shRNA, or dsRNA.

In further embodiments, a method for obtaining a nucleic acid fragment comprising a polynucleotide for producing a substantial portion of an iRNA (e.g., dsRNA, siRNA, miRNA, shRNA, and hpRNA) molecule includes: (a) synthesizing first and second oligonucleotide primers specifically complementary to a portion of a native polynucleotide from a targeted hemipteran pest; and (b) amplifying a cDNA or gDNA insert present in a cloning vector using the first and second oligonucleotide primers of step (a), wherein the amplified nucleic acid molecule comprises a substantial portion of a siRNA, miRNA, hpRNA, mRNA, shRNA, or dsRNA molecule.

Nucleic acids of the invention can be isolated, amplified, or produced by a number of approaches. For example, an iRNA (e.g., dsRNA, siRNA, miRNA, shRNA, and hpRNA) molecule may be obtained by PCR amplification of a target polynucleotide (e.g., a target gene or a target transcribed non-coding polynucleotide) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present invention may be produced chemically or enzymatically by one skilled in the art through manual or automated reactions, or in vivo in a cell comprising a nucleic acid molecule comprising a polynucleotide encoding the RNA, dsRNA, siRNA, miRNA, shRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3

RNA polymerase, T7 RNA polymerase, and SP6 RNA polymerase). Expression constructs useful for the cloning and expression of polynucleotides are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In particular embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a hemipteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a polynucleotide that, upon expression to RNA and ingestion by a hemipteran pest, achieves suppression of a target gene in a cell, tissue, or organ of the pest. Thus, some embodiments provide a recombinant nucleic acid molecule comprising a polynucleotide capable of being expressed as an iRNA (e.g., dsRNA, siRNA, miRNA, shRNA, and hpRNA) molecule in a plant cell to inhibit target gene expression in a hemipteran pest. In order to initiate or enhance expression, such recombinant nucleic acid molecules may comprise one or more regulatory elements, which regulatory elements may be operably linked to the polynucleotide capable of being expressed as an iRNA. Methods to express a gene suppression molecule in plants are known, and may be used to express a polynucleotide of the present invention. See, e.g., International PCT Publication No. WO06/073727; and U.S. Patent Publication No. 2006/0200878 A1)

In specific embodiments, a recombinant DNA molecule of the invention may comprise a polynucleotide encoding an RNA that may form a dsRNA molecule. Such recombinant DNA molecules may encode RNAs that may form dsRNA molecules capable of inhibiting the expression of endogenous target gene(s) in a hemipteran pest cell upon ingestion. In many embodiments, a transcribed RNA may form a dsRNA molecule that may be provided in a stabilized form; e.g., as a hairpin and stem and loop structure.

In other embodiments, one strand of a dsRNA molecule may be formed by transcription from a polynucleotide that is substantially homologous to a polynucleotide selected from the group consisting of SEQ ID NO:1; the complement of SEQ ID NO:1; a fragment of at least 15 contiguous nucleotides of SEQ ID NO:1; the complement of a fragment of at least 15 contiguous nucleotides of SEQ ID NO:1; a native coding polynucleotide of a hemipteran organism (e.g., BSB) comprising any of SEQ ID NOs:1, 3, and 4; the complement of a native coding polynucleotide of a hemipteran organism comprising any of SEQ ID NOs:1, 3, and 4; a fragment of at least 15 contiguous nucleotides of a native coding polynucleotide of a hemipteran organism comprising any of SEQ ID NOs:1, 3, and 4; and the complement of a fragment of at least 15 contiguous nucleotides of a native coding polynucleotide of a hemipteran organism comprising any of SEQ ID NOs:1, 3, and 4.

In particular embodiments, a recombinant DNA molecule encoding an RNA that may form a dsRNA molecule may comprise a coding region wherein at least two polynucleotides are arranged such that one polynucleotide is in a sense orientation, and the other polynucleotide is in an antisense orientation, relative to at least one promoter, wherein the sense polynucleotide and the antisense polynucleotide are linked or connected by a spacer of, for example, from about five (~5) to about one thousand (~1000) nucleotides. The spacer may form a loop between the sense and antisense polynucleotides. The sense polynucleotide or the antisense polynucleotide may be substantially homologous to an RNA encoded by a target gene (e.g., a kruppel gene comprising SEQ ID NO:1) or fragment thereof. In some embodiments, however, a recombinant DNA molecule may encode an RNA that may form a dsRNA molecule without a spacer. In embodiments, a sense coding polynucleotide and an antisense coding polynucleotide may be different lengths.

Polynucleotides identified as having a deleterious effect on hemipteran pests or a plant-protective effect with regard to hemipteran pests may be readily incorporated into expressed dsRNA molecules through the creation of appropriate expression cassettes in a recombinant nucleic acid molecule of the invention. For example, such polynucleotides may be expressed as a hairpin with stem and loop structure by taking a first segment corresponding to an RNA encoded by a target gene polynucleotide (e.g., a kruppel gene comprising SEQ ID NO:1, and fragments of either of the foregoing); linking this polynucleotide to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms comprising the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native hemipteran pest polynucleotide is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Certain embodiments of the invention include introduction of a recombinant nucleic acid molecule of the present invention into a plant (i.e., transformation) to achieve hemipteran pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acids of the invention can, for example, be suitably inserted into a vector under the control of a suitable promoter that functions in one or more hosts to drive expression of a linked coding polynucleotide or other DNA element. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart protection from hemipteran pests to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a polynucleotide that is substantially homologous and specifically hybridizable to a corresponding transcribed polynucleotide within a hemipteran pest that may cause damage to the host plant species. The hemipteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within hemipteran pests that infest the transgenic host plant. In some embodiments, suppression of expression of the target gene in the target hemipteran pest may result in the plant being tolerant to attack by the pest.

In order to enable delivery of iRNA molecules to a hemipteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a polynucleotide of the invention operably linked to one or more regulatory elements, such as a heterologous promoter element that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a leaf-specific promoter or pollen-specific promoter. In some embodiments, a polynucleotide or fragment for hemipteran pest control according to the invention may be cloned between two tissue-specific promoters oriented in opposite transcriptional directions relative to the polynucleotide or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a hemipteran pest so that suppression of target gene expression is achieved.

Additional regulatory elements that may optionally be operably linked to a nucleic acid molecule of interest include 5'UTRs located between a promoter element and a coding polynucleotide that function as a translation leader element. The translation leader element is present in the fully-processed mRNA, and it may affect processing of the primary transcript, and/or RNA stability. Examples of translation leader elements include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank™ Accession No. V00087; and Bevan et al. (1983) Nature 304:184-7).

Additional regulatory elements that may optionally be operably linked to a nucleic acid molecule of interest also include 3' non-translated elements, 3' transcription termination regions, or polyadenylation regions. These are genetic elements located downstream of a polynucleotide, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation element can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory elements operatively linked to one or more polynucleotides of the present invention. When expressed, the one or more polynucleotides result in one or more RNA molecule(s) comprising a polynucleotide that is specifically complementary to all or part of a native RNA molecule in a hemipteran pest. Thus, the polynucleotide(s) may comprise a segment encoding all or part of a polyribonucleotide present within a targeted hemipteran pest RNA transcript, and may comprise inverted repeats of all or a part of a targeted pest transcript. A plant transformation vector may contain polynucleotides specifically complementary to more than one target polynucleotide, thus allowing production of more than one dsRNA for inhibiting expression of two or more genes in cells of one or more populations or species of target hemipteran pests. Segments of polynucleotides specifically complementary to polynucleotides present in different genes can be combined into a single composite nucleic acid molecule for expression in a transgenic plant. Such segments may be contiguous or separated by a spacer.

In other embodiments, a plasmid of the present invention already containing at least one polynucleotide(s) of the invention can be modified by the sequential insertion of additional polynucleotide(s) in the same plasmid, wherein the additional polynucleotide(s) is/are operably linked to the same regulatory elements as the original at least one polynucleotide(s). In some embodiments, a nucleic acid molecule may be designed for the inhibition of multiple target genes. In some embodiments, the multiple genes to be inhibited can be obtained from the same hemipteran pest species, which may enhance the effectiveness of the nucleic acid molecule. In other embodiments, the genes can be derived from different hemipteran pests, which may broaden the range of pests against which the agent(s) is/are effective. When multiple genes are targeted for suppression or a combination of expression and suppression, a polycistronic DNA element can be engineered.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide tolerance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate tolerance; a nitrilase gene which confers resistance to bromoxynil; a mutant acetolactate synthase (ALS) gene which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In $18^{th}$ *Stadler Genetics Symposium*, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to hemipteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acids encoding one or more iRNA molecules in the genome of the transgenic plant.

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border elements. The T-region may also contain a selectable marker for efficient recovery of transgenic cells and plants, and a multiple cloning site for inserting polynucleotides for transfer such as a dsRNA encoding nucleic acid.

In some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent No. EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA encoding one or more iRNA molecules that inhibit target gene expression in a hemipteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of gDNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to gDNA derived from any plant species (e.g., *Z. mays, G. max*, and *Gossypium* sp.) or tissue type, including cell cultures.

A transgenic plant formed using *Agrobacterium*-dependent transformation methods typically contains a single recombinant DNA inserted into one chromosome. The polynucleotide of the single recombinant DNA is referred to as a "transgenic event" or "integration event." Such transgenic plants are heterozygous for the inserted exogenous polynucleotide. In some embodiments, a transgenic plant homozygous with respect to a transgene may be obtained by sexually mating (selfing) an independent segregant transgenic plant that contains a single exogenous gene to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using a SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have a hemipteran pest-inhibitory effect. The iRNA molecules (e.g., dsRNA molecules) may be expressed from multiple nucleic acids introduced in different transformation events, or from a single nucleic acid introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple polynucleotides that are each homologous to different loci within one or more hemipteran pests (for example, the loci defined by SEQ ID NO:1), both in different populations of the same species of hemipteran pest, or in different species of hemipteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a polynucleotide that encodes an iRNA molecule may be introduced into a first plant line that is amenable to transformation to produce a transgenic plant, which transgenic plant may be crossed with a second plant line to introgress the polynucleotide that encodes the iRNA molecule into the second plant line.

The invention also includes commodity products containing one or more of the polynucleotides of the present invention. Particular embodiments include commodity products produced from a recombinant plant or seed containing one or more of the polynucleotides of the present invention.

A commodity product containing one or more of the polynucleotides of the present invention is intended to include, but not be limited to, meals, oils, crushed or whole grains or seeds of a plant, or any food product comprising any meal, oil, or crushed or whole grain of a recombinant plant or seed containing one or more of the polynucleotides of the present invention. The detection of one or more of the polynucleotides of the present invention in one or more commodity or commodity products contemplated herein is de facto evidence that the commodity or commodity product is produced from a transgenic plant designed to express one or more of the polynucleotides of the present invention for the purpose of controlling plant pests using dsRNA-mediated gene suppression methods.

In some aspects, seeds and commodity products produced by transgenic plants derived from transformed plant cells are included, wherein the seeds or commodity products comprise a detectable amount of a nucleic acid of the invention. In some embodiments, such commodity products may be produced, for example, by obtaining transgenic plants and preparing food or feed from them. Commodity products comprising one or more of the polynucleotides of the invention includes, for example and without limitation: meals, oils, crushed or whole grains or seeds of a plant, and any food product comprising any meal, oil, or crushed or whole grain of a recombinant plant or seed comprising one or more of the nucleic acids of the invention. The detection of one or more of the polynucleotides of the invention in one or more commodity or commodity products is de facto evidence that the commodity or commodity product is produced from a transgenic plant designed to express one or more of the iRNA molecules of the invention for the purpose of controlling hemipteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a hemipteran pest other than the ones defined by SEQ ID NO:1; a transgenic event from which is transcribed an iRNA molecule targeting a gene in an organism other than a hemipteran pest (e.g., a plant-parasitic nematode); a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility. In particular embodiments, polynucleotides encoding iRNA molecules of the invention may be combined with other insect control and disease traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Hemipteran Pest

A. Overview

In some embodiments of the invention, at least one nucleic acid molecule useful for the control of hemipteran pests may be provided to a hemipteran pest, wherein the nucleic acid molecule leads to RNAi-mediated gene silencing in the pest(s). In particular embodiments, an iRNA molecule (e.g., dsRNA, siRNA, miRNA, shRNA, and hpRNA) may be provided to the hemipteran host. In some embodiments, a nucleic acid molecule useful for the control of hemipteran pests may be provided to a pest by contacting the nucleic acid molecule with the pest. In these and further embodiments, a nucleic acid molecule useful for the control of hemipteran pests may be provided in a feeding substrate of the pest, for example, a nutritional composition. In these and further embodiments, a nucleic acid molecule useful for the control of a hemipteran pest may be provided through ingestion of plant material comprising the nucleic acid molecule that is ingested by the pest(s). In certain embodiments, the nucleic acid molecule is present in plant material through expression of a recombinant nucleic acid introduced into the plant material, for example, by transformation of a plant cell with a vector comprising the recombinant nucleic acid and regeneration of a plant material or whole plant from the transformed plant cell.

B. RNAi-mediated Target Gene Suppression

In particular embodiments, the invention provides iRNA molecules (e.g., dsRNA, siRNA, miRNA, shRNA, and hpRNA) that may be designed to target essential native polynucleotides (e.g., essential genes) in the transcriptome of a hemipteran (e.g., BSB) pest, for example by designing an iRNA molecule that comprises at least one strand comprising a polynucleotide that is specifically complementary to the target polynucleotide. The sequence of an iRNA molecule so designed may be identical to that of the target polynucleotide, or may incorporate mismatches that do not prevent specific hybridization between the iRNA molecule and its target polynucleotide.

iRNA molecules of the invention may be used in methods for gene suppression in a hemipteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding polynucleotide including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In some embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand." The passenger strand may be degraded, and the guide strand may be incorporated into RISC. Post-transcriptional inhibition occurs by specific hybridization of the guide strand with a specifically complementary polynucleotide of an mRNA molecule, and subsequent cleavage by the enzyme, Argonaute (catalytic component of the RISC complex).

In other embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a polynucleotide, which polynucleotide may be expressed in vitro to produce an iRNA molecule that is substantially homologous to a nucleic acid molecule encoded by a polynucleotide within the genome of a hemipteran pest. In certain embodiments, the in vitro transcribed iRNA molecule may be a stabilized dsRNA molecule that comprises a stem-loop structure. After a hemipteran pest contacts the in vitro transcribed iRNA molecule, post-transcriptional inhibition of a target gene in the pest (for example, an essential gene) may occur.

In some embodiments of the invention, expression of an iRNA from a nucleic acid molecule comprising at least 15 contiguous nucleotides (e.g., at least 19 contiguous nucleotides) of a polynucleotide are used in a method for post-transcriptional inhibition of a target gene in a hemipteran pest, wherein the polynucleotide is selected from the group consisting of: SEQ ID NO:1; the complement of SEQ ID NO:1; a fragment of at least 15 contiguous nucleotides of SEQ ID NO:1 (e.g., SEQ ID NO:3 and SEQ ID NO:4); the complement of a fragment of at least 15 contiguous nucleotides of SEQ ID NO:1; a native coding polynucleotide of a hemipteran organism comprising any of SEQ ID NOs:1, 3, and 4; the complement of a native coding polynucleotide of a hemipteran organism comprising any of SEQ ID NOs:1, 3, and 4; a fragment of at least 15 contiguous nucleotides of a native coding polynucleotide of a hemipteran organism comprising any of SEQ ID NOs:1, 3, and 4; and the complement of a fragment of at least 15 contiguous nucleotides of a native coding polynucleotide of a hemipteran organism comprising any of SEQ ID NOs:1, 3, and 4. In certain embodiments, expression of a nucleic acid molecule that is at least about 80% identical (e.g., 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a hemipteran pest.

It is an important feature of some embodiments herein that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., polynucleotides substantially homologous to the iRNA molecule(s) are targeted for genetic inhibition. In some embodiments, an RNA molecule comprising a polynucleotide with a nucleotide sequence that is identical to that of a portion of a target gene may be used for inhibition. In these and further embodiments, an RNA molecule comprising a polynucleotide with one or more insertion, deletion, and/or point mutations relative to a target polynucleotide may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length polynucleotide exhibiting a greater homology compensates for a longer, less homologous polynucleotide. The length of the polynucleotide of a duplex region of a dsRNA molecule that is identical to a portion of a target gene transcript may be at least about 25, 50, 100, 200, 300, 400, 500, or at least about 1000 bases. In some embodiments, a polynucleotide of greater than 20-100 nucleotides may be used, for example, a polynucleotide of 100-200 or 300-500 nucleotides may be used. In particular embodiments, a polynucleotide of greater than about 200-300 nucleotides may be used. In particular embodiments, a polynucleotide of greater than about 500-1000 nucleotides may be used, depending on the size of the target gene.

In certain embodiments, expression of a target gene in a hemipteran pest may be inhibited by at least 10%; at least 33%; at least 50%; or at least 80% within a cell of the pest, such that a significant inhibition takes place. Significant inhibition refers to inhibition over a threshold that results in a detectable phenotype (e.g., cessation of reproduction, feeding, development, etc.), or a detectable decrease in RNA and/or gene product corresponding to the target gene being inhibited. Although in certain embodiments of the invention inhibition occurs in substantially all cells of the pest, in other embodiments inhibition occurs only in a subset of cells expressing the target gene.

In some embodiments, transcriptional suppression is mediated by the presence in a cell of a dsRNA molecule exhibiting substantial sequence identity to a promoter DNA or the complement thereof to effect what is referred to as "promoter trans suppression." Gene suppression may be effective against target genes in a hemipteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary polynucleotides in the cells of the hemipteran pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of RNAi Molecules Provided to a Hemipteran Pest

Expression of iRNA molecules for RNAi-mediated gene inhibition in a hemipteran pest may be carried out in any one of many in vitro or in vivo formats. The iRNA molecules may then be provided to a hemipteran pest, for example, by contacting the iRNA molecules with the pest, or by causing the pest to ingest or otherwise internalize the iRNA molecules. Some embodiments of the invention include transformed host plants of a hemipteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a hemipteran pest during feeding, the pest may ingest iRNA molecules expressed in the transgenic plants or cells. The polynucleotides of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a hemipteran pest comprises providing in the tissue of the host of the pest a gene-suppressive amount of at least one dsRNA molecule formed following transcription of a polynucleotide as described herein, at least one segment of which is complementary to an mRNA within the cells of the hemipteran pest. A dsRNA molecule, including its modified form such as an siRNA, miRNA, shRNA, or hpRNA molecule, ingested by a hemipteran pest in accordance with the invention may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from a kruppel DNA molecule, for example, comprising a polynucleotide selected from the group consisting of SEQ ID NOs:1, 3, and 4. Isolated and substantially purified nucleic acid molecules including, but not limited to, non-naturally occurring polynucleotides and recombinant DNA constructs for providing dsRNA molecules of the present invention are therefore provided, which suppress or inhibit the expression of an endogenous coding polynucleotide or a target coding polynucleotide in the hemipteran pest when introduced thereto.

Particular embodiments provide a delivery system for the delivery of iRNA molecules for the post-transcriptional inhibition of one or more target gene(s) in a hemipteran plant pest and control of a population of the plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acids encoding a particular iRNA molecule may be produced by employing recombinant DNA technologies (which basic technologies are well-known in the art) to construct a plant transformation vector comprising a polynucleotide encoding an iRNA molecule of the invention (e.g., a stabilized dsRNA molecule); to transform a plant cell or plant; and to generate the transgenic plant cell or the transgenic plant that contains the transcribed iRNA molecule.

To impart protection from hemipteran pests to a transgenic plant, a recombinant DNA molecule may, for example, be transcribed into an iRNA molecule, such as a dsRNA molecule, an siRNA molecule, an miRNA molecule, an shRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a polynucleotide that is identical to a corresponding polynucleotide transcribed from a DNA within a hemipteran pest of a type that may infest the host plant. Expression of a target gene within the hemipteran pest is suppressed by the dsRNA molecule, and the suppression of expression of the target gene in the hemipteran pest results in the transgenic plant being resistant to the pest. The modulatory effects of dsRNA molecules have been shown to be applicable to a variety of genes expressed in pests, including, for example, endogenous genes responsible for cell division, chromosomal remodeling, and cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a polynucleotide for use in producing iRNA molecules may be operably linked to one or more promoter elements functional in a plant host cell. The promoter may be an endogenous promoter, normally resident in the host genome. The polynucleotide of the present invention, under the control of an operably linked promoter element, may further be flanked by additional elements that advantageously affect its transcription and/or the stability of a resulting transcript. Such elements may be located upstream of the operably linked promoter, downstream of the 3' end of the expression construct, and may occur both upstream of the promoter and downstream of the 3' end of the expression construct.

In embodiments, suppression of a target gene (e.g., a kruppel gene) results in a parental RNAi phenotype; a phenotype that is observable in progeny of the subject (e.g., a hemipteran pest) contacted with the iRNA molecule. In some embodiments, the pRNAi phenotype comprises the pest being rendered less able to produce viable offspring. In particular examples of pRNAi, a nucleic acid that initiates pRNAi does not increase the incidence of mortality in a population into which the nucleic acid is delivered. In other examples of pRNAi, a nucleic acid that initiates pRNAi also increases the incidence of mortality in a population into which the nucleic acid is delivered.

In some embodiments, a population of hemipteran pests is contacted with an iRNA molecule, thereby resulting in pRNAi, wherein the pests survive and mate but produce eggs that are less able to hatch viable progeny than eggs produced by pests of the same species that are not provided the nucleic acid(s). In some examples, such pests do not oviposit eggs or oviposit fewer eggs than what is observable in pests of the same species that are not contacted with the iRNA molecule. In some examples, the eggs oviposited by such pests do not hatch or hatch at a rate that is significantly less than what is observable in pests of the same species that are not contacted with the iRNA molecule. In some examples, the nymphs that hatch from eggs oviposited by such pests are not viable or are less viable than what is observable in pests of the same species that are not contacted with the iRNA molecule.

Transgenic crops that produce substances that provide protection from insect feeding are vulnerable to adaptation by the target insect pest population reducing the durability of the benefits of the insect protection substance(s). Traditionally, delays in insect pest adaptation to transgenic crops are achieved by (1) the planting of "refuges" (crops that do not contain the pesticidal substances, and therefore allow survival of insects that are susceptible to the pesticidal substance(s)); and/or (2) combining insecticidal substances with multiple modes of action against the target pests, so that individuals that are resistant to one mode of action are killed by a second mode of action.

In some examples, iRNA molecules (e.g., expressed from a transgene in a host plant) represent new modes of action for combining with *Bacillus thuringiensis* insecticidal protein technology and/or lethal RNAi technology in Insect Resistance Management gene pyramids to mitigate against the development of insect populations resistant to either of these control technologies.

Parental RNAi may result in some embodiments in a type of pest control that is different from the control obtained by lethal RNAi, and which may be combined with lethal RNAi to result in synergistic pest control. Thus, in particular embodiments, iRNA molecules for the post-transcriptional inhibition of one or more target gene(s) in a hemipteran plant pest can be combined with other iRNA molecules to provide redundant RNAi targeting and synergistic RNAi effects.

Parental RNAi (pRNAi) that causes egg mortality or loss of egg viability has the potential to bring further durability benefits to transgenic crops that use RNAi and other mechanisms for insect protection. pRNAi prevents exposed insects from producing progeny, and therefore from passing on to the next generation any alleles they carry that confer resistance to the pesticidal substance(s). pRNAi is particularly useful in extending the durability of insect-protected transgenic crops when it is combined with one or more additional pesticidal substances that provide protection from the same pest populations. Such additional pesticidal substances may in some embodiments include, for example, nymph-active dsRNA; insecticidal proteins (such as those derived from *Bacillus thuringiensis* or other organisms); and other insecticidal substances. This benefit arises because insects that are resistant to the pesticidal substances occur as a higher proportion of the population in the transgenic crop than in the refuge crop. If a ratio of resistance alleles to susceptible alleles that are passed on to the next generation is lower in the presence of pRNAi than in the absence of pRNAi, the evolution of resistance will be delayed.

For example, pRNAi may not reduce the number of individuals in a first pest generation that are inflicting damage on a plant expressing an iRNA molecule. However, the ability of such pests to sustain an infestation through subsequent generations may be reduced. Conversely, lethal RNAi may kill pests that already are infesting the plant. When pRNAi is combined with lethal RNAi, pests that are contacted with a parental iRNA molecule may breed with pests from outside the system that have not been contacted with the iRNA, however, the progeny of such a mating may be non-viable or less viable, and thus may be unable to infest the plant. At the same time, pests that are contacted with a lethal iRNA molecule may be directly affected. The combination of these two effects may be synergistic; i.e., the combined pRNAi and lethal RNAi effect may be greater than the sum of the pRNAi and lethal RNAi effects independently. pRNAi may be combined with lethal RNAi, for example, by providing a plant that expresses both lethal and parental iRNA molecules; by providing in the same location a first plant that expresses lethal iRNA molecules and a second plant that expresses parental iRNA molecules; and/or by contacting pests with the pRNAi molecule, and subsequently releasing the contacted pests into the plant environment, such that they can mate unproductively with the plant pests.

Some embodiments provide methods for reducing the damage to a host plant (e.g., a soybean plant) caused by a hemipteran pest that feeds on the plant, wherein the method comprises providing in the host plant a transformed plant cell expressing at least one nucleic acid molecule of the invention, wherein the nucleic acid molecule(s) functions upon being taken up by the pest(s) to inhibit the expression of a target polynucleotide within the pest(s), which inhibition of expression results in reduced reproduction, for example, in addition to mortality and/or reduced growth of the pest(s), thereby reducing the damage to the host plant caused by the pest(s). In some embodiments, the nucleic acid molecule(s) comprise dsRNA molecules. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consist of one polynucleotide that is specifically hybridizable to a nucleic acid molecule expressed in a hemipteran pest cell.

In other embodiments, a method for increasing the yield of a corn crop is provided, wherein the method comprises introducing into a corn plant at least one nucleic acid molecule of the invention; and cultivating the corn plant to allow the expression of an iRNA molecule comprising the nucleic acid, wherein expression of an iRNA molecule comprising the nucleic acid inhibits hemipteran pest damage and/or growth, thereby reducing or eliminating a loss of yield due to hemipteran pest infestation. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consists of one polynucleotide that is specifically hybridizable to a nucleic acid molecule expressed in a hemipteran pest cell.

In some embodiments, a method for increasing the yield of a plant crop is provided, wherein the method comprises introducing into a female hemipteran pest (e.g, by injection, by ingestion, by spraying, and by expression from a DNA) at least one nucleic acid molecule of the invention; and releasing the female pest into the crop, wherein mating pairs including the female pest are unable or less able to produce viable offspring, thereby reducing or eliminating a loss of yield due to hemipteran pest infestation. In particular embodiments, such a method provides control of subsequent generations of the pest. In similar embodiments, the method comprises introducing the nucleic acid molecule of the invention into a male hemipteran pest, and releasing the male pest into the crop (e.g., wherein pRNAi male pests produce less sperm than untreated controls). In some embodiments, the nucleic acid molecule is a DNA molecule that is expressed to produce an iRNA molecule. In some embodiments, the nucleic acid molecule is a dsRNA molecule. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consists of one polynucleotide that is specifically hybridizable to a nucleic acid molecule expressed in a hemipteran pest cell.

In some embodiments, a method for modulating the expression of a target gene in a hemipteran pest is provided, the method comprising: transforming a plant cell with a vector comprising a polynucleotide encoding at least one iRNA molecule of the invention, wherein the polynucleotide is operatively-linked to a promoter and a transcription termination element; culturing the transformed plant cell under conditions sufficient to allow for development of a plant cell culture including a plurality of transformed plant cells; selecting for transformed plant cells that have integrated the polynucleotide into their genomes; screening the transformed plant cells for expression of an iRNA molecule encoded by the integrated polynucleotide; selecting a transgenic plant cell that expresses the iRNA molecule; and feeding the selected transgenic plant cell to the hemipteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consists of one polynucleotide that is specifically hybridizable to a nucleic acid molecule expressed in a hemipteran pest cell.

iRNA molecules of the invention can be incorporated within the seeds of a plant species (e.g., soybean), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to hemipteran pests. For example, the iRNA molecules of the invention may be directly introduced into the cells of a pest(s). Methods for introduction may include direct mixing of iRNA into the diet of the hemipteran pest (e.g., by mixing with plant tissue from a host for the pest), as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the hemipteran pests known to infest the plant. iRNA molecules produced by chemical or enzymatic synthesis may also be formulated in a manner consistent with common agricultural practices, and used as spray-on products for controlling plant damage by a hemipteran pest. The formulations may include the appropriate adjuvants (e.g., stickers and wetters) required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from hemipteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1

RNAi Constructs

Template Preparation by PCR and dsRNA Synthesis

The strategies used to provide specific templates for kruppel dsRNA production are shown in FIG. 1A and FIG. 1B. Template DNAs intended for use in kruppel dsRNA synthesis are prepared by PCR using specific primers and first-strand cDNA prepared from total RNA. For kruppel selected target gene regions, two separate PCR amplifications are performed. FIG. 1. The first PCR amplification introduces a T7 promoter sequence at the 5' end of the amplified sense strands. The second reaction incorporates the T7 promoter sequence at the 5' ends of the antisense strands. The two PCR amplified fragments for each region of the target genes are then mixed in approximately equal amounts, and the mixture is used as transcription template for dsRNA production. FIG. 1.

For the YFP negative control, a single PCR amplification was performed. FIG. 1B. The PCR amplification introduced a T7 promoter sequence at the 5' ends of the amplified sense and antisense strands. The two PCR amplified fragments for each region of the target genes were then mixed in approximately equal amounts, and the mixture was used as transcription template for dsRNA production. FIG. 1B. dsRNA for the negative control YFP coding region (SEQ ID NO:6) was produced using specific primers and a DNA clone of the YFP coding region as template. The PCR product amplified for kruppel and YFP were used as a template for in vitro synthesis of dsRNAs using the MEGAscript high-yield transcription kit (Applied Biosystems Inc., Foster City, Calif.). The synthesized dsRNAs were purified using the RNeasy Mini kit (Qiagen, Valencia, Calif.) or an AMBION® MEGAscript® RNAi kit, essentially as prescribed by the manufacturer's instructions. dsRNA preparations were quantified using a NANODROP™ 8000 spectrophotometer (THERMO SCIENTIFIC, Wilmington, Del.) or equivalent means, and analyzed by gel electrophoresis to determine purity.

Example 2

Real-time PCR Analysis

Quantitative Real-Time PCR: Relative expression levels of transcripts are analyzed by probe hydrolysis quantitative Real-Time PCR (qPCR) using Roche LightCycler480. The PCR primers and hydrolysis probes are designed using LightCycler Probe Design Software 2.0 (Roche). dsRNA-injected insects or eggs are frozen on dry ice. Tissue disruption is performed with a Klecko™ tissue pulverizer (Garcia Manufacturing, Visalia, Calif.) in the kit RLT lysis buffer with one stainless steel bead. Following tissue maceration, the total RNA is isolated in high throughput format using the RNeasy96® kit (Qiagen, #74182) following the kit protocol with the optional on column DNaseI treatment step at ½× suggested concentration for 30 minutes and additional DNaseI digest using Turbo™ DNase (AM2238, Life Technologies, Carlsbad Calif.) for 1 hour at room temperature on the elutant.

First-strand cDNA synthesis for High-Throughput qPCR assay: High capacity cDNA RT kit (part#4368813. Life technologies, Carlsbad Calif.) is used according to manufacturer supplied protocol with the following modifications. Total RNA is adjusted to ~10 ng/μL with nuclease-free water. RNA samples (5 μL, or no more than 250 ng total RNA) is heated to 70° C. for 10 minutes and cooled to 4° C. Half reactions are initiated by addition of 5 μL of 2× mix. The primer mix, which is supplied solely as random primers, is first spiked with custom synthesized $T_{20}VN$ oligo (Integrated DNA Technologies, Coralville Iowa) to a final concentration of 2 μM, in order to improve the sensitivity of 3'UTR based assays. Following first strand synthesis, the samples are diluted 1:3 with nuclease free water and stored at −20° C. until ready to be assayed by high-throughput (HTP) qPCR.

Non-injected insects and YFP dsRNA-injected insects are used as controls. The BSB Actin (Act) (SEQ ID NO:18) is used as a reference gene (Ponton et al. (2011) J Insect Physiol 57 (6):840-50). The primers and probes for the experimental and reference genes appear in Table 1.

TABLE 1

Oligonucleotides and probes for BSB probe hydrolysis qPCR assay

| Reference GENE | NAME | SEQUENCE |
|---|---|---|
| Actin | Actin-F | TCAAGGAAAAACTGTGCTATGT (SEQ ID NO: 19) |
| Actin | Actin-R | TACCGATGGTGATGACCTGA (SEQ ID NO: 20) |
| Actin | Actin-FAM | ACCGCCGCTGCC (SEQ ID NO: 21) |

Example 3

Construction of Plant Transformation Vectors

An entry vector harboring a target gene construct for dsRNA hairpin formation comprising segments of kruppel (SEQ ID NO:1) is assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a target gene segment in opposite orientation to one another, the two segments being separated by a linker sequence (e.g. ST-LS1 intron, SEQ ID NO:7; Vancanneyt et al. (1990) Mol. Gen. Genet. 220:245-250). Thus, the primary mRNA transcript contains the two kruppel gene segment sequences as large inverted repeats of one another, separated by the linker sequence. A copy of a promoter (e.g. maize ubiquitin 1, U.S. Pat. No. 5,510,474; 35S from Cauliflower Mosaic Virus (CaMV); promoters from rice actin genes; ubiquitin promoters; pEMU; MAS; maize H3 histone promoter; ALS promoter; phaseolin gene promoter; cab; rubisco; LAT52; Zm13; and/or apg) is used to drive production of the primary mRNA hairpin transcript, and a fragment comprising a 3' untranslated region, for example and without limitation, a maize peroxidase 5 gene (ZmPer5 3'UTR v2; U.S. Pat. No. 6,699,984), AtUbi10, AtEf1, or StPinII is used to terminate transcription of the hairpin-RNA-expressing gene.

The entry vector described above is used in standard GATEWAY® recombination reactions with a typical binary destination vector to produce kruppel hairpin RNA expression transformation vectors for Agrobacterium-mediated plant embryo transformations.

A negative control binary vector which comprises a gene that expresses a YFP hairpin dsRNA is constructed by means of standard GATEWAY® recombination reactions with a typical binary destination vector and entry vector. The entry vector comprises a YFP hairpin sequence under the expression control of a maize ubiquitin 1 promoter and a fragment comprising a 3' untranslated region from a maize peroxidase 5 gene.

A binary destination vector comprises a herbicide tolerance gene (aryloxyalknoate dioxygenase; (AAD-1 v3, U.S. Pat. No. 7,838,733, and Wright et al. (2010) Proc. Natl. Acad. Sci. U.S.A. 107:20240-5)) under the regulation of a plant operable promoter (e.g., sugarcane bacilliform badnavirus (ScBV) promoter (Schenk et al. (1999) Plant Mol. Biol. 39:1221-30) or ZmUbi1 (U.S. Pat. No. 5,510,474)). 5' UTR and intron from these promoters, are positioned between the 3' end of the promoter segment and the start codon of the AAD-1 coding region. A fragment comprising a 3' untranslated region from a maize lipase gene (ZmLip 3'UTR; U.S. Pat. No. 7,179,902) is used to terminate transcription of the AAD-1 mRNA.

A further negative control binary vector that comprises a gene that expresses a YFP protein, is constructed by means of standard GATEWAY® recombination reactions with a typical binary destination vector and entry vector. The binary destination vector comprises a herbicide tolerance gene (aryloxyalknoate dioxygenase; AAD-1 v3) (as above) under the expression regulation of a maize ubiquitin 1 promoter and a fragment comprising a 3' untranslated region from a maize lipase gene (ZmLip 3'UTR). The entry vector comprises a YFP coding region under the expression control of a maize ubiquitin 1 promoter and a fragment comprising a 3' untranslated region from a maize peroxidase 5 gene.

Example 4

Insect Rearing and Candidate Gene Selection in Neotropical Brown Stink Bug (Euschistus heros)

Insect rearing. Neotropical Brown Stink Bugs (BSB; Euschistus heros) were reared in a 27° C. incubator, at 65% relative humidity, with 16:8 hour light:dark cycle. One gram of eggs collected over 2-3 days was seeded in 5 L containers with filter paper discs at the bottom; the containers were covered with #18 mesh for ventilation. Each rearing container yielded approximately 300-400 adult BSB. At all stages, the insects were fed fresh green beans three times per week and a sachet of seed mixture containing sunflower seeds, soybeans, and peanuts (3:1:1 by weight ratio) was replaced once a week. Water was supplemented in vials with cotton plugs as wicks. After the initial two weeks, insects were transferred to a new container once a week.

RNAi target selection. Six stages of BSB development were selected for mRNA library preparation. Total RNA was extracted from insects frozen at −70° C. and homogenized in 10 volumes of Lysis/Binding buffer in Lysing MATRIX A 2 mL tubes (MP BIOMEDICALS, Santa Ana, Calif.) on a FastPrep®-24 Instrument (MP BIOMEDICALS). Total mRNA was extracted using a mirVana™ miRNA Isolation Kit (AMBION; INVITROGEN) according to the manufacturer's protocol. RNA sequencing using an Illumina® HiSeq™ system (San Diego, Calif.) provided candidate target gene sequences for use in RNAi insect control technology. HiSeq™ generated a total of about 378 million reads for the six samples. Reads were assembled individually for each sample using TRINITY assembler software (Grabherr et al. (2011) Nature Biotech. 29:644-652). The assembled transcripts were combined to generate a pooled transcriptome. This BSB pooled transcriptome contains 378,457 sequences.

E. heros kruppel ortholog identification. A tBLASTn search of the E. heros pooled transcriptome was performed using sequences of the Drosophila KRUPPEL (Kr-PA, GENBANK Accession No. NP_523867) protein. E. heros kruppel (SEQ ID NO:1) was identified as a Euschistus heros candidate target gene The sequence of SEQ ID NO:1 is novel. There was no significant homologous nucleotide sequence found with a search in GENBANK. The closest homolog of the Diabrotica KRUPPEL amino acid sequence (SEQ ID NO:2) is a Oncopeltus fasciatus protein having GENBANK Accession No. AAT44519.1 (82% similar; 78% identical over the homology region).

Template preparation and dsRNA synthesis. cDNA was prepared from total BSB RNA extracted from a single young adult insect (about 90 mg) using TRIzol® Reagent (LIFE TECHNOLOGIES, Grand Island, N.Y.). The insect was homogenized at room temperature in a 1.5 mL microcentrifuge tube with 200 µL of TRIzol® using a pellet pestle (FISHERBRAND, Grand Island, N.Y.) and Pestle Motor Mixer (COLE-PARMER, Vernon Hills, Ill.). Following homogenization, an additional 800 µL of TRIzol® was added, the homogenate was vortexed, and then incubated at room temperature for five minutes. Cell debris was removed by centrifugation and the supernatant was transferred to a new tube. Following manufacturer-recommended TRIzol® extraction protocol for 1 mL of TRIzol®, the RNA pellet was dried at room temperature and resuspended in 200 µL Tris Buffer from a GFX PCR DNA AND GEL EXTRACTION KIT (Illustra™; GE HEALTHCARE LIFE SCIENCES, Pittsburgh, Pa.) using Elution Buffer Type 4 (i.e. 10 mM Tris-HCl pH8.0). RNA concentration was determined using a NANODROP™ 8000 spectrophotometer (THERMO SCIENTIFIC, Wilmington, Del.).

cDNA was reverse-transcribed from 5 µg BSB total RNA template and oligo dT primer using a SUPERSCRIPT III FIRST-STRAND SYNTHESIS SYSTEM™ for RT-PCR (INVITROGEN), following the supplier's recommended protocol. The final volume of the transcription reaction was brought to 100 µL with nuclease-free water.

Primers for BSB_kr-1, dsRNA BSB_kr-1-F (SEQ ID NO:8) and BSB_kr-1-R (SEQ ID NO:9), were used to amplify DNA templates for dsRNA transcription. Primers for BSB_kr-2, dsRNA BSB_kr-2-F (SEQ ID NO:10) and BSB_kr-2-R (SEQ ID NO:11), were used to amplify DNA templates for dsRNA transcription. The DNA templates were amplified using "touch-down" PCR (annealing temperature lowered from 60° C. to 50° C. in a 1° C./cycle decrease) with 1 µL of cDNA (above) as the template. Fragments comprising a 434 bp segment of BSB_kr-1 (SEQ ID NO:3) and a 605 bp segment BSB_kr-2 (SEQ ID NO:4) were generated during 35 cycles of PCR. The above procedure was used to amplify a 301 bp negative control template YFPv2 (SEQ ID NO:12) using primers YFPv2_F (SEQ ID NO:13) and YFPv2_R (SEQ ID NO:14). The BSB-specific and YFPv2 primers contained a T7 phage promoter sequence (SEQ ID NO:5) at their 5' ends, enabling the use of the aforementioned BSB DNA fragments for dsRNA transcription.

dsRNAs were synthesized using 2 µL of PCR product (above) as the template with a MEGAscript™ RNAi kit (AMBION) or HiScribe® T7 In Vitro Transcription Kit, used according to the manufacturer's instructions. See FIG. 1. dsRNA was quantified on a NANODROP™ 8000 spectrophotometer and diluted to 1 µg/µL in nuclease-free 0.1× TE buffer (1 mM Tris HCL, 0.1 mM EDTA, pH 7.4).

Example 5 dsRNA Injection into $2^{nd}$ Instar Neotropical Brown Stink Bug (*Euschistus heros*) Nymphs BSB artificial diet. BSB artificial diet was prepared as follows and used within two weeks of preparation. Lyophilized green beans were blended to a fine powder in a MAGIC BULLET® blender while raw (organic) peanuts were blended in a separate MAGIC BULLET® blender. Blended dry ingredients were combined (weight percentages: green beans, 35%; peanuts, 35%; sucrose, 5%; Vitamin complex (e.g. Vanderzant Vitamin Mixture for insects, SIGMA-ALDRICH), 0.9%); in a large MAGIC BULLET® blender, which was capped and shaken well to mix the ingredients. The mixed dry ingredients were then added to a mixing bowl. In a separate container, water and benomyl anti-fungal agent (50 ppm; 25 µL 20,000 ppm solution/50 mL diet solution) were mixed well and then added to the dry ingredient mixture. All ingredients were mixed by hand until the solution was fully blended. The diet was shaped into desired sizes, wrapped loosely in aluminum foil, heated for 4 hours at 60° C., then cooled and stored at 4° C.

Injection of dsRNA into BSB hemocoel. BSB were reared on a green bean and seed diet, as the colony described above, in a 27° C. incubator at 65% relative humidity and 16:8 hour light:dark photoperiod. Second instar nymphs (each weighing 1 to 1.5 mg) were gently handled with a small brush to prevent injury and were placed in a Petri dish on ice to chill and immobilize the insects. Each insect was injected with 55.2 nL of a 500 ng/µL dsRNA solution (i.e., 27.6 ng dsRNA; dosage of 18.4 to 27.6 µg/g body weight). Injections were performed using a NANOJECT™ II injector (DRUMMOND SCIENTIFIC, Broomhall, Pa.) equipped with an injection needle pulled from a Drummond 3.5 inch #3-000-203-G/X glass capillary. The needle tip was broken and the capillary was backfilled with light mineral oil, then filled with 2 to 3 µL of dsRNA. dsRNA was injected into the abdomen of the nymphs (10 insects injected per dsRNA per trial), and the trials were repeated on three different days. Injected insects (5 per well) were transferred into 32-well trays (Bio-RT-32 Rearing Tray; BIO-SERV, Frenchtown, N.J.) containing a pellet of artificial BSB diet and covered with Pull-N-Peel™ tabs (BIO-CV-4; BIO-SERV). Moisture was supplied by means of 1.25 mL water in a 1.5 mL microcentrifuge tube with a cotton wick. The trays were incubated at 26.5° C., 60% humidity and 16:8 hour light:dark photoperiod. Viability counts and weights were taken on day 7 after the injections.

Injection of dsRNA that targets kruppel mRNA in BSB $2^{nd}$ instar nymphs.

dsRNA homologous to a YFP coding region, YFPv2, was used as a negative control in BSB injection experiments. As summarized in Table 2, 27.6 ng BSB_kr-1 dsRNA injected into the hemocoel of $2^{nd}$ instar BSB did not lead to increased mortality within seven days.

TABLE 2

Results of *E. heros* kruppel dsRNA injection into the hemocoel of 2$^{nd}$ instar *E. heros* nymphs seven days after injection. Table shows mean percent mortality, N number of trials, standard error of the mean (SEM) and a p-value of two-tailed student t-test.

| Treatment | Mean % mortality | SEM | N trials | t-test (p) |
| --- | --- | --- | --- | --- |
| BSB_kr-1 | 20 | 5.8 | 3 | 2.88E−01 |
| Not injected | 13 | 3.3 | 3 | 6.43E−01 |
| YFPv2 dsRNA | 10 | 5.8 | 3 | |

Example 6

Egg Hatch Following dsRNA Injection in *Euschistus heros*

Injection of dsRNA into adult BSB hemocoel. BSB were reared as described above for the colony. In the following exemplification, young adults (zero to three days post adult molt) were collected and chilled in a secondary container on ice. The females and males were separated based on structural dimorphism of the genitalia. Female BSB were handled with featherweight entomology forceps and injected with dsRNA using a NANOJECT™ II injector (DRUMMOND SCIENTIFIC, Broomhall, Pa.) equipped with an injection needle pulled from a Drummond 3.5 inch #3-000-203-G/X glass capillary. The needle tip was broken and the capillary was backfilled with light mineral oil then filled with 3 μL dsRNA. Ten to twenty females (approximately 90 mg each) per treatment were injected with dsRNA. Each female was injected into the abdomen twice consecutively with 69 nL 1 μg/μL dsRNA for a total of 138 nL (138 ng). Each batch of ten females was moved into a 1 quart (~950 mL) bin with an opening in the lid and #18 mesh for ventilation. Two adult males were added to each bin of ten females. The insects were supplied with a vial of water, green beans, and seeds as described in the rearing procedure. The insects were kept at 26.5° C., 60% humidity and 16:8 light:dark photoperiod.

Surviving female counts, oviposited eggs and egg hatch numbers were collected on a daily basis starting at nine days after injection and continued for up to 24 days. Eggs were removed daily and kept in Petri dishes or multi-well plates on a layer of 1% agarose in water. Fresh green beans were supplied to adults every other day. The adult insects were transferred into bins with fresh water and food every week.

Females injected with dsRNA that targets a 301 nt sequence (SEQ ID NO:12) of the YFP coding region were used as a negative control and compared to un-injected and females injected with BSB_kr-1 (SEQ ID NO:3) dsRNA.

Injections of dsRNA targeting kruppel in BSB females has no significant effect on oviposition. As summarized in Table 3 kruppel dsRNA-injected females oviposited somewhat lower numbers of eggs from YFPv2 dsRNA injected and not injected controls. The average # of eggs oviposited/day/female (Table 3) was not significantly different from the YFP control. There was a surprising and unexpected overall hatch rate from females treated with kruppel dsRNA. The total number of eggs hatched were dramatically reduced in all replications, ranging from 10% to 31%, as compared to 89% hatch rate for YFPv2 (Table 4).

TABLE 3

Number of eggs oviposited per female per day in three replicates of BSB_kr-1 dsRNA application. Ten to twenty females were injected with dsRNA targeted against BSB kruppel or negative control YFPv2. Egg counts encompass 14 days of collection, starting at day 11 post injection. Two-tailed paired t-tests were performed in Excel.

| dsRNA | total # of eggs oviposited | mean # of eggs/day/female | Std. Deviation | Std. Error | t-test (p) |
| --- | --- | --- | --- | --- | --- |
| Kr-1 rep.1 | 662 | 5.65 | 1.46 | 0.390 | 5.87E−01 |
| Kr-1 rep.2 | 742 | 6.01 | 1.68 | 0.450 | 9.56E−01 |
| Kr-1 rep.3 | 385 | 4.99 | 2.18 | 0.583 | 2.23E−01 |
| YFPv2 | 904 | 5.98 | 1.47 | 0.393 | |

TABLE 4

Number of BSB eggs hatched per female per day based on the eggs oviposited in Table 3. Eggs were collected on daily basis, with most hatching on days 5, 6, and 7 after collection. Two-tailed paired t-tests were performed in Excel for mean # hatched/day/female.

| dsRNA | total # of eggs hatched | % egg hatch | mean # eggs hatched/day/female | Std. Deviation | Std. Error | t-test (p) |
| --- | --- | --- | --- | --- | --- | --- |
| Kr-1 rep. 1 | 65 | 10% | 0.66 | 0.98 | 0.261 | 1.67E−06* |
| Kr-1 rep. 2 | 133 | 18% | 1.15 | 0.93 | 0.249 | 8.91E−06* |
| Kr-1 rep. 3 | 120 | 31% | 1.91 | 1.40 | 0.373 | 1.72E−04* |
| YFPv2 | 805 | 89% | 5.30 | 1.46 | 0.391 | |

*indicates significant difference (p-value < 0.05)

Example 7

Transgenic *Zea mays* Comprising Hemipteran Pest Sequences

Ten to 20 transgenic T$_0$ *Zea mays* plants harboring expression vectors for nucleic acids comprising SEQ ID NO:1, SEQ ID NO:3, and/or SEQ ID NO:4 are generated as described in EXAMPLE 3. A further 10-20 T$_1$ *Zea mays* independent lines expressing hairpin dsRNA for an RNAi construct are obtained for BSB challenge. Hairpin dsRNA may be derived comprising a segment of SEQ ID NO:1. These are confirmed through RT-PCR or other molecular analysis methods. Total RNA preparations from selected independent T$_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect hemipterans in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, reproduction, and viability of feeding hemipteran pests.

In planta delivery of dsRNA, siRNA, shRNA, hpRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and/or reproduction of the hemipteran pest is affected, and in the case of at least one of *Euschistus heros, Piezodorus guildinii, Halyomorpha halys, Nezara viridula, Acrosternum hilare*, and *Euschistus serous* leads to failure to successfully infest, feed, develop, and/or reproduce, or leads to death of the hemipteran pest. The choice of target genes and the successful application of RNAi is then used to control hemipteran pests.

Phenotypic comparison of transgenic RNAi lines and non-transformed *Zea mays.*

Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 8

Transgenic *Glycine max* Comprising Hemipteran Pest Sequences

Ten to 20 transgenic To *Glycine max* plants harboring expression vectors for nucleic acids comprising SEQ ID NO:1 or a segment of SEQ ID NO:1 are generated as is known in the art, including for example by *Agrobacterium*-mediated transformation, as follows. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of split-seed soybeans. The split soybean seed comprising a portion of an embryonic axis protocol requires preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of *Agrobacterium tumefaciens* (e.g., strain EHA 101 or EHA 105) containing binary plasmid comprising SEQ ID NO:1, SEQ ID NO:3 and/or SEQ ID NO:4. The *Agrobacterium tumefaciens* solution is diluted to a final concentration of $\lambda$=0.6 $OD_{650}$ before immersing the cotyledons comprising the embryo axis.

Co-cultivation. Following inoculation, the split soybean seed is allowed to co-cultivate with the *Agrobacterium tumefaciens* strain for 5 days on co-cultivation medium (*Agrobacterium* Protocols, vol. 2, $2^{nd}$ Ed., Wang, K. (Ed.) Humana Press, New Jersey, 2006) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L $Na_2$EDTA, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2$EDTA, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SII medium supplemented with 6 mg/L glufosinate (LIBERTY®).

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2$EDTA, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 μmol/$m^2$ sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2$EDTA, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/$m^2$ sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

A further 10-20 T1 *Glycine max* independent lines expressing hairpin dsRNA for an RNAi construct are obtained for BSB challenge. Hairpin dsRNA may be derived as set forth in SEQ ID NOs:3 and 4, or otherwise further comprising SEQ ID NO:1. These are confirmed through RT-PCR or other molecular analysis methods, as known in the art. Total RNA preparations from selected independent T₁ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Glycine max* plant. Processing of the dsRNA hairpin of the target genes into siRNA is subsequently optionally confirmed in independent transgenic lines using RNA blot hybridizations.

RNAi molecules having mismatch sequences with more than 80% sequence identity to target genes affect BSB in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, reproduction, and viability of feeding hemipteran pests.

In planta delivery of dsRNA, siRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and/or reproduction of the hemipteran pest is affected, and in the case of at least one of *Euschistus heros, Piezodorus guildinii, Halyomorpha halys, Nezara viridula, Acrosternum hilare*, and *Euschistus* serous leads to failure to successfully infest, feed, develop, and/or reproduce, or leads to death of the hemipteran pest. The choice of target genes and the successful application of RNAi is then used to control hemipteran pests.

Phenotypic comparison of transgenic RNAi lines and non-transformed *Glycine max*. Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 9

*E. heros* Bioassays on Artificial Diet

In dsRNA feeding assays on artificial diet, 32-well trays are set up with an ~18 mg pellet of artificial diet and water, as for injection experiments. dsRNA at a concentration of 200 ng/μL is added to the food pellet and water sample, 100 μL to each of two wells. Five $2^{nd}$ instar *E. heros* nymphs are introduced into each well. Water samples and dsRNA that targets YFP transcript are used as negative controls. The experiments are repeated on three different days. Surviving insects are weighed and the mortality rates are determined after 7 days of treatment.

Feeding bioassays on adult female *E. heros* are performed as 32-well trays as described above. Young (less than one week of adulthood) mated females are introduced into bioassay trays with artificial diet, one per tray. After 7 days of exposure to dsRNA up to ten adult females are moved to containers with green beans, water, seeds, and two males. Female viability as well as the numbers of eggs oviposited and eggs hatched are recorded for the following two weeks. The data shows that the numbers of eggs oviposited and/or hatched are significantly reduced.

Example 10

Transgenic *Arabidopsis thaliana* Comprising Hemipteran Pest Sequences

*Arabidopsis* transformation vectors containing a target gene construct for hairpin formation comprising segments of kruppel (SEQ ID NO:1) are generated using standard molecular methods similar to EXAMPLE 4. *Arabidopsis* transformation is performed using standard *Agrobacterium*-based procedure. $T_1$ seeds are selected with glufosinate tolerance selectable marker. Transgenic $T_1$ *Arabidopsis* plants are generated and homozygous simple-copy T2 transgenic plants are generated for insect studies. Bioassays are performed on growing *Arabidopsis* plants with inflorescences. Five to ten insects are placed on each plant and monitored for survival within 14 days.

Construction of *Arabidopsis* transformation vectors. Entry clones based on an entry vector harboring a target gene construct for hairpin formation comprising a segment of kruppel (SEQ ID NO:1) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a target gene segment in opposite orientations, the two segments being separated by an linker sequence (e.g. ST-LS1 intron; SEQ ID NO:7) (Vancanneyt et al. (1990) Mol. Gen. Genet. 220(2):245-50). Thus, the primary mRNA transcript contains the two kruppel gene segment sequences as large inverted repeats of one another, separated by the linker sequence. A copy of a promoter (e.g. *Arabidopsis thaliana* ubiquitin 10 promoter (Callis et al. (1990) J. Biological Chem. 265:12486-12493)) is used to drive production of the primary mRNA hairpin transcript, and a fragment comprising a 3' untranslated region from Open Reading Frame 23 of *Agrobacterium tumefaciens* (AtuORF23 3' UTR v1; U.S. Pat. No. 5,428,147) is used to terminate transcription of the hairpin-RNA-expressing gene.

The hairpin clone within the entry vector described above is used in standard GATEWAY® recombination reaction with a typical binary destination vector to produce hairpin RNA expression transformation vectors for *Agrobacterium*-mediated *Arabidopsis* transformation.

The binary destination vector comprises a herbicide tolerance gene, DSM-2v2 (U.S. Patent App. No. 2011/0107455), under the regulation of a Cassava vein mosaic virus promoter (CsVMV Promoter v2, U.S. Pat. No. 7,601,885; Verdaguer et al. (1996) Plant Mol. Biol. 31:1129-39). A fragment comprising a 3' untranslated region from Open Reading Frame 1 of *Agrobacterium tumefaciens* (AtuORF1

3' UTR v6; Huang et al. (1990) J. Bacteriol. 172:1814-22) is used to terminate transcription of the DSM2v2 mRNA.

A negative control binary construct, which comprises a gene that expresses a YFP hairpin RNA, is constructed by means of standard GATEWAY® recombination reactions with a typical binary destination vector and entry vector. An entry construct comprises a YFP hairpin sequence (SEQ ID NO:6) under the expression control of an *Arabidopsis* Ubiquitin 10 promoter (as above) and a fragment comprising an ORF23 3' untranslated region from *Agrobacterium tumefaciens* (as above).

Production of transgenic *Arabidopsis* comprising insecticidal hairpin RNAs: *Agrobacterium*-mediated transformation. Binary plasmids containing hairpin sequences are electroporated into *Agrobacterium* strain GV3101 (pMP90RK). The recombinant *Agrobacterium* clones are confirmed by restriction analysis of plasmids preparations of the recombinant *Agrobacterium* colonies. A Qiagen Plasmid Max Kit (Qiagen, Cat#12162) is used to extract plasmids from *Agrobacterium* cultures following the manufacture recommended protocol.

*Arabidopsis* transformation and $T_1$ selection. Twelve to fifteen *Arabidopsis* plants (c.v. Columbia) are grown in 4" pots in the green house with light intensity of 250 µmol/m², 25° C., and 18:6 hours of light:dark conditions. Primary flower stems are trimmed one week before transformation. *Agrobacterium* inoculums are prepared by incubating 10 µL recombinant *Agrobacterium* glycerol stock in 100 mL LB broth (Sigma L3022)+100 mg/L Spectinomycin+50 mg/L Kanamycin at 28° C. and shaking at 225 rpm for 72 hours. *Agrobacterium* cells are harvested and suspended into 5% sucrose+0.04% Silwet-L77 (Lehle Seeds Cat # VIS-02)+10 µg/L benzamino purine (BA) solution to $OD_{600}$ 0.8-1.0 before floral dipping. The above-ground parts of the plant are dipped into the *Agrobacterium* solution for 5-10 minutes, with gentle agitation. The plants are then transferred to the greenhouse for normal growth with regular watering and fertilizing until seed set.

Example 11

Growth and Bioassays of Transgenic *Arabidopsis*

Selection of $T_1$ *Arabidopsis* transformed with hairpin RNAi constructs. Up to 200 mg of $T_1$ seeds from each transformation are stratified in 0.1% agarose solution. The seeds are planted in germination trays (10.5"×21"×1"; T.O. Plastics Inc., Clearwater, Minn.) with #5 sunshine media. Transformants are selected for tolerance to Ignite® (glufosinate) at 280 g/ha at 6 and 9 days post planting. Selected events are transplanted into 4" diameter pots. Insertion copy analysis is performed within a week of transplanting via hydrolysis quantitative Real-Time PCR (qPCR) using Roche LightCycler480™. The PCR primers and hydrolysis probes are designed against DSM2v2 selectable marker using LightCycler™ Probe Design Software 2.0 (Roche). Plants are maintained at 24° C., with a 16:8 hour light:dark photoperiod under fluorescent and incandescent lights at intensity of 100-150 mE/m²s.

*E. heros* nymph plant feeding bioassay. At least four low copy (1-2 insertions), four medium copy (2-3 insertions), and four high copy (≥4 insertions) events are selected for each construct. Plants are grown to a reproductive stage (plants containing flowers and siliques). The surface of soil is covered with ~50 mL volume of white sand for easy insect identification. Five to ten $2^{nd}$ instar *E. heros* nymphs are introduced onto each plant. The plants are covered with plastic tubes that are 3" in diameter, 16" tall, and with wall thickness of 0.03" (Item No. 484485, Visipack Fenton MO); the tubes are covered with nylon mesh to isolate the insects. The plants are kept under normal temperature, light, and watering conditions in a conviron. In 14 days, the insects are collected and weighed; percent mortality as well as growth inhibition (1−weight treatment/weight control) are calculated. YFP hairpin-expressing plants are used as controls.

*E. heros* adults plant feeding bioassay. The pRNAi *Arabidopsis* $T_1$ plants are selected and grown in greenhouse, as described above. One to 5 newly emerged BSB adults are released on each plant and the entire plant is covered as described above to prevent adults from escaping. One week after release, female adults are recovered from each plant and maintained in the laboratory for egg collection. Depending on the parental RNAi target and expected phenotype, parameters such as number of eggs per female, percent egg hatch and nymph mortality are recorded and compared with control plants.

T2 *Arabidopsis* seed generation and T2 bioassays. T2 seed is produced from selected low copy (1-2 insertions) events for each construct. Plants (homozygous and/or heterozygous) are subjected to *E. heros* nymph and adult feeding bioassay, as described above. T3 seed is harvested from homozygotes and stored for future analysis.

Example 12

Transformation of Additional Crop Species

Cotton is transformed with kruppel (with or without a chloroplast transit peptide) to provide control of stink bugs by utilizing a method known to those of skill in the art, for example, substantially the same techniques previously described in EXAMPLE 14 of U.S. Pat. No. 7,838,733, or Example 12 of PCT International Patent Publication No. WO 2007/053482.

Example 13 pRNAi-mediated Insect Protection

Parental RNAi that causes egg mortality or loss of egg viability brings further durability benefits to transgenic crops that use RNAi and other mechanisms for insect protection. A basic two-patch model was used to demonstrate this utility.

One patch contained a transgenic crop expressing insecticidal ingredients, and the second patch contained a refuge crop not expressing insecticidal ingredients. Eggs were oviposited in the two modeled patches according to their relative proportions. In this example, the transgenic patch represented 95% of the landscape, and the refuge patch represented 5%. The transgenic crop expressed an insecticidal protein active against the insect.

Pest to the insecticidal protein was modeled as monogenic, with two possible alleles; one (S) conferring susceptibility, and the other (R) conferring resistance. The insecticidal protein was modeled to cause 97% mortality of homozygous susceptible (SS) nymphs that feed on it. There was assumed to be no mortality of nymphs that are homozygous for the resistance allele (RR). Resistance to the insecticidal protein was assumed to be incompletely recessive, whereby the functional dominance is 0.3 (there is 67.9% mortality of nymphs that are heterozygous (RS) for resistance to the protein that feed on the transgenic crop).

The transgenic crop also expressed parentally active dsRNA that, through RNA-interference (pRNAi), causes the eggs of adult female insects that are exposed to the transgenic crop to be non-viable. Insect resistance to the pRNAi was also considered to be monogenic with two possible alleles; one (X) conferring susceptibility of the adult female to RNAi, and the other (Y) conferring resistance of the adult female to RNAi. Assuming a high level of exposure to the dsRNAs, the pRNAi was modeled to cause 99.9% of eggs produced by a homozygous susceptible (XX) female to be non-viable. The model assumed that pRNAi has no effect on the viability of eggs produced by homozygous resistant (YY) females. Resistance to the dsRNA was assumed to be recessive, whereby the functional dominance is 0.01 (98.9% of eggs produced by a female that is heterozygous (XY) for resistance to dsRNA are non-viable).

In the model, there was random mating among surviving adults and random oviposition across the two patches in accordance with their relative proportions. The genotypic frequencies of viable offspring followed Mendelian genetics for a two-locus genetic system.

The effect of pRNAi required the adult females to feed on plant tissue expressing parental active dsRNA. The interference with egg development may be lower for adult females emerging from the refuge crop than from the transgenic crop; adults may feed more extensively in the patch in which they emerged following nymph development. Therefore, the relative magnitude of the pRNAi effect on female adults emerging from the refuge patch was varied, with the proportion of the pRNAi effect ranging from 0 (no effect of pRNAi on adult females emerging from the refuge patch) to 1 (same effect of pRNAi on adult females emerging from the refuge patch as on adult females emerging from the transgenic patch).

This model could be easily adjusted to demonstrate the situation when the effect of pRNAi is also or alternatively achieved by feeding of adult males on plant tissue expressing parental active dsRNA.

Figure 3:
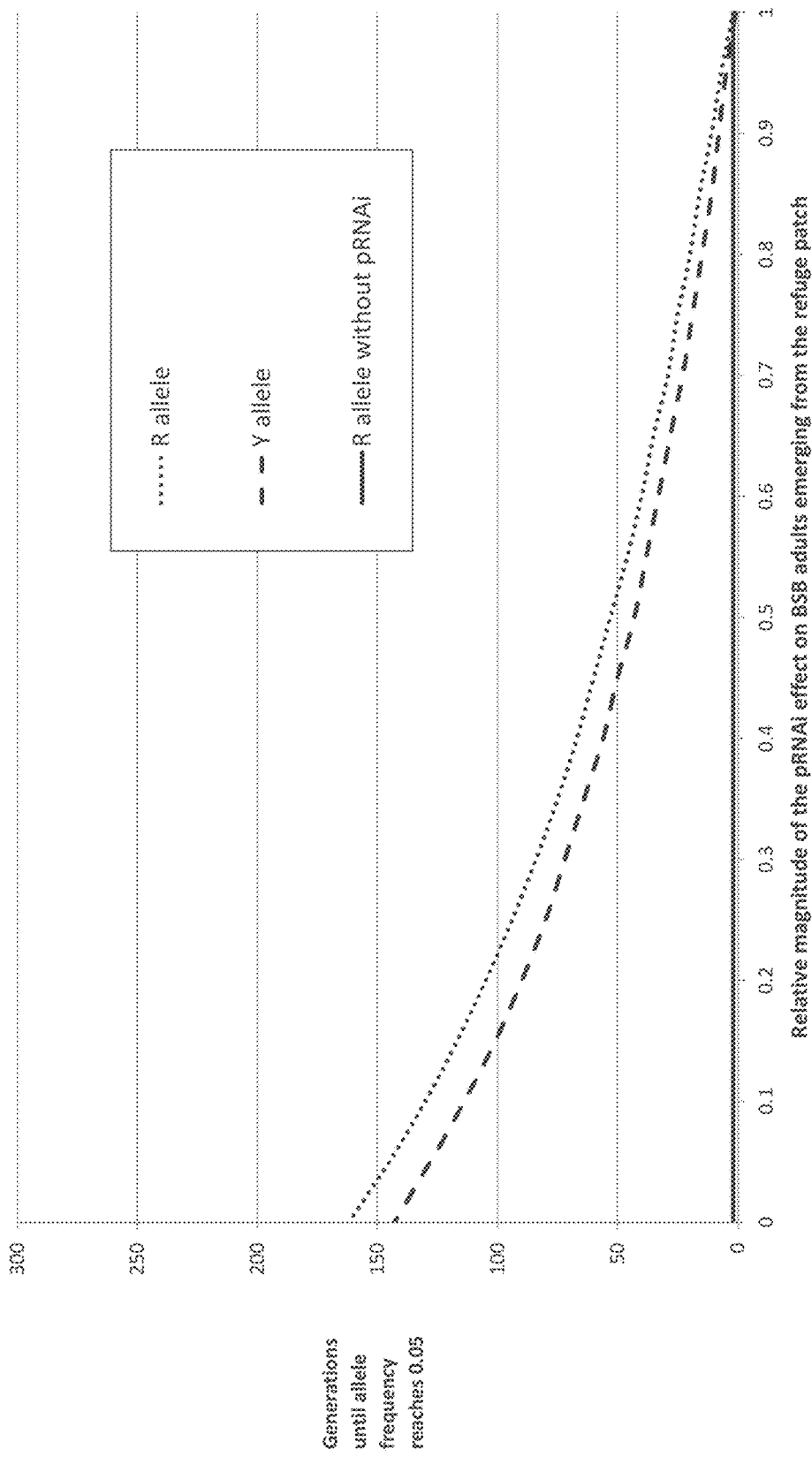
FIG. 3 includes a summary of modeling data showing the effect of relative magnitude of a pRNAi effect on female BSB adults emerging from a "refuge patch" (i.e., that did not express insecticidal iRNAs or recombinant proteins in a transgenic crop) on the rate of increase in allele frequencies for resistance to an insecticidal protein (R) and RNAi (Y) when non-refuge plants express the insecticidal protein and parental active iRNA.

Frequencies of the two resistance alleles were calculated across generations. The initial frequencies of both of the resistance alleles (R and Y) were assumed to be 0.005. Results were presented as the number of insect generations for the frequencies of each of the resistance alleles to reach 0.05. To examine the resistance delay caused by the pRNAi, simulations that included pRNAi were compared to simulations that did not include pRNAi, but were identical in every other way. FIG. 3.

Figure 4:
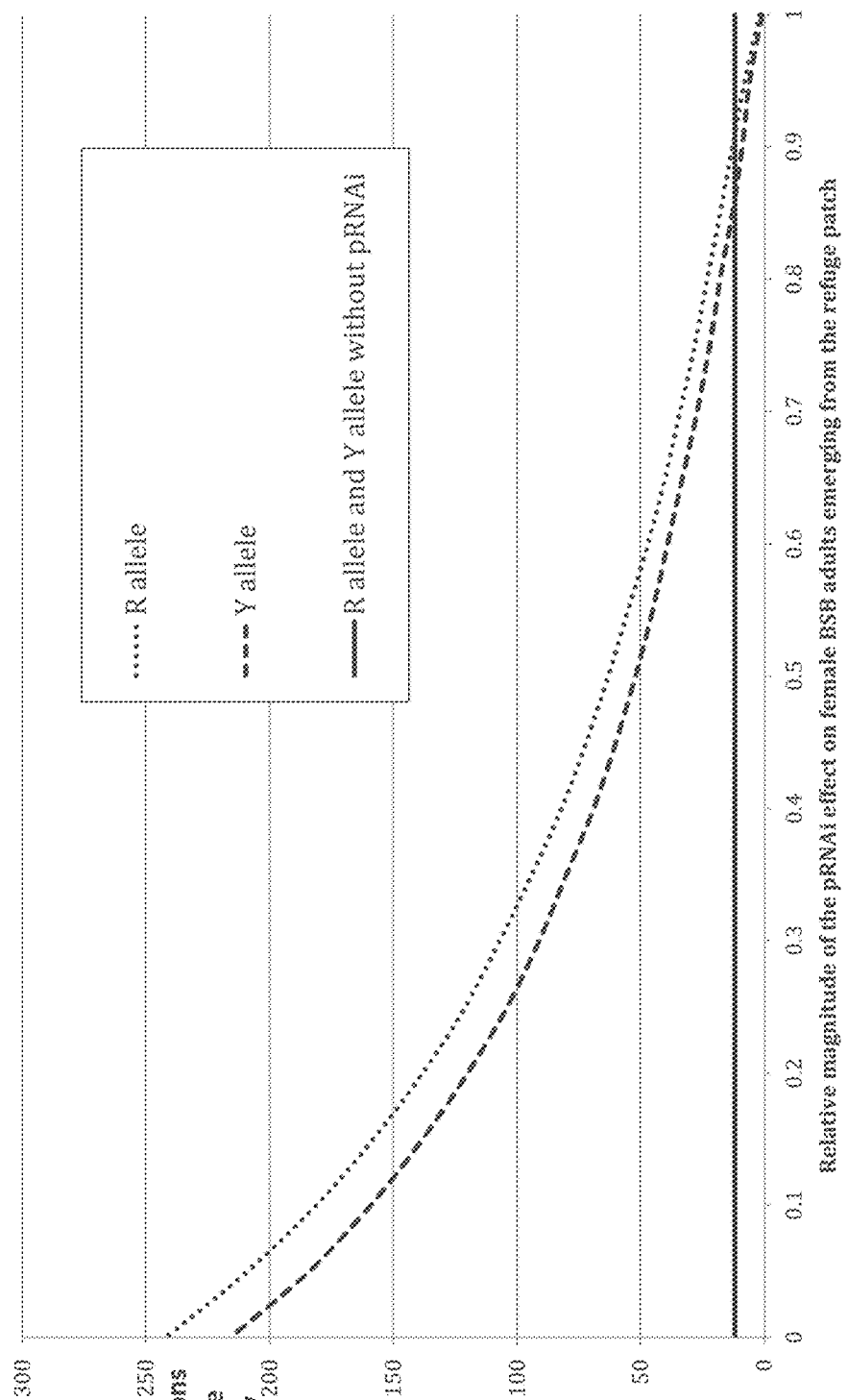
FIG. 4 includes a summary of modeling data showing the effect of relative magnitude of a pRNAi effect on female BSB adults emerging from a "refuge patch" (i.e., that did not express insecticidal iRNAs or recombinant proteins in a transgenic crop of plants comprising BSB nymph-active interfering dsRNA in combination with the BSB-active insecticidal protein in the transgenic crop) on the rate of increase in allele frequencies for resistance to an insecticidal protein (R) and RNAi (Y) when non-refuge plants express the insecticidal protein and both larval active and parental active iRNA molecules.

The model was also modified to include nymph-active interfering dsRNA in combination with the insecticidal protein in the transgenic crop. Therein, the nymph RNAi was assigned an effect of 97% nymph mortality for homozygous RNAi-susceptible nymphs (genotype XX), and no effect on nymphs that are homozygous RNAi-resistant (YY). There was 67.9% mortality of nymphs that were heterozygous for RNAi-resistance (XY). It was assumed that the same mechanism of resistance applied to both nymph active RNAi and pRNAi. As before, the pRNAi effect on adult females emerging from the refuge patch relative to the effect on adult females emerging from the transgenic patch was varied from 0 to 1. As before, to examine the resistance delay caused by the pRNAi, simulations that included pRNAi were compared to simulations that did not include pRNAi, but were identical in every other way (including nymph RNAi). FIG. 4.

A clear resistance management benefit of pRNAi was observed when the magnitude of the pRNAi effect on egg viability for female adults emerging from the refuge patch was reduced compared with magnitude of the effect for adults emerging from the transgenic patch. The transgenic crops that produced parental active dsRNA in addition to an insecticidal protein were much more durable compared with transgenic crops that produced only an insecticidal protein. Similarly, transgenic crops that produced parental active dsRNA in addition to both an insecticidal protein and a nymph active dsRNA were much more durable compared with transgenic crops that produced only an insecticidal protein and a nymph active dsRNA. In the latter case, the durability benefit applied to both the insecticidal protein and the insecticidal interfering dsRNA.

Example 14

Transgenic Plants Comprising a Hemipteran Pest Sequence and Additional RNAi Constructs A transgenic plant comprising a heterologous coding sequence in its genome that is transcribed into an iRNA molecule that targets an organism other than a hemipteran pest is secondarily transformed via *Agrobacterium* or WHISKERS™ methodologies (See Petolino and Arnold (2009) Methods Mol. Biol. 526:59-67) to produce one or more insecticidal dsRNA molecules (for example, at least one dsRNA molecule including a dsRNA molecule targeting a gene comprising SEQ ID NO:1). Plant transformation plasmid vectors prepared essentially as described in EXAMPLE 3 are delivered via *Agrobacterium* or WHISKERS™-mediated transformation methods into suspension cells or immature embryos obtained from a transgenic plant comprising a heterologous coding sequence in its genome that is transcribed into an iRNA molecule that targets an organism other than a hemipteran pest.

Example 15

Transgenic Plants Comprising an RNAi Construct and Additional Hemipteran Pest Control Sequences A transgenic plant comprising a heterologous coding sequence in its genome that is transcribed into an iRNA molecule that targets a hemipteran pest organism (for example, at least one dsRNA molecule including a dsRNA molecule targeting a gene comprising SEQ ID NO:1) is secondarily transformed via *Agrobacterium* or WHISKERS™ methodologies (see Petolino and Arnold (2009) Methods Mol. Biol. 526:59-67) to produce one or more insecticidal protein molecules, for example, Cry3, Cry34 and Cry35 insecticidal proteins. Plant transformation plasmid vectors prepared essentially as described in EXAMPLE 3 are delivered via *Agrobacterium* or WHISKERS™-mediated transformation methods into suspension cells or immature embryos obtained from a transgenic plant comprising a heterologous coding sequence in its genome that is transcribed into an iRNA molecule that targets a hemipteran pest organism. Doubly-transformed plants are obtained that produce iRNA molecules and insecticidal proteins for control of hemipteran pests.

What may be claimed is:

1. An isolated nucleic acid molecule comprising a polynucleotide operably linked to a heterologous promoter, wherein the polynucleotide encodes a double-stranded ribonucleic acid (dsRNA) molecule, the polynucleotide comprising:
   a first nucleotide sequence selected from the group consisting of SEQ ID NO:1, the complement of SEQ ID NO: 1, at least 23 contiguous nucleotides of SEQ ID NO:1, the complement of at least 23 contiguous nucleotides of SEQ ID NO:1, native coding sequence of Euschistus heros comprising SEQ ID NO:1, the complement of a native coding sequence of Euschistus heros comprising SEQ ID NO:1, at least 23 contiguous nucleotides of a native coding sequence of Euschistus heros comprising SEQ ID NO:1, and the complement of at least 23 contiguous nucleotides of a native coding sequence of Euschistus heros comprising SEQ ID NO:1;
   a second nucleotide sequence; and
   a third nucleotide sequence that is the reverse complement of the first nucleotide sequence,
   wherein the third nucleotide sequence is operably linked to the first nucleotide sequence by the second nucleotide sequence.

2. The nucleic acid molecule of claim 1, wherein the first nucleotide sequence is selected from the group consisting of SEQ ID NO:3 and SEQ ID NO:4.

3. The nucleic acid molecule of claim 1, wherein the heterologous promoter is functional in a plant cell.

4. The nucleic acid molecule of claim 3, wherein the first nucleotide sequence comprises at least 23 contiguous nucleotides of SEQ ID NO: 1 or the complement of at least 23 contiguous nucleotides of SEQ ID NO:1.

5. A double-stranded ribonucleic acid (dsRNA) molecule comprising a first, a second, and a third ribonucleotide sequence,
- wherein the first ribonucleotide sequence is encoded by a nucleotide sequence selected from the group consisting of SEQ ID NO:1, the complement of SEQ ID NO:1, at least 23contiguous nucleotides of SEQ ID NO:1, the complement of at least 23 contiguous nucleotides of SEQ ID NO:1, a native coding sequence of *Euschistus heros* comprising SEQ ID NO:1, the complement of a native coding sequence of *Euschistus heros* comprising SEQ ID NO:1, at least 23 contiguous nucleotides of a native coding sequence of *Euschistus heros* comprising SEQ ID NO:1, and the complement of at least 23 contiguous nucleotides of a native coding sequence of *Euschistus heros* comprising SEQ ID NO:1,
- wherein the third ribonucleotide sequence is linked to the first ribonucleotide sequence by the second ribonucleotide sequence, and
- wherein the third ribonucleotide sequence is the reverse complement of the first ribonucleotide sequence, such that the first and the third ribonucleotide sequences hybridize to form the stem of a hairpin structure in the molecule.

6. The RNA molecule of claim 5, wherein the first nucleotide sequence is encoded by at least 23 contiguous nucleotides of SEQ ID NO: 1 or the complement of at least 23 contiguous nucleotides of SEQ ID NO:1.

7. The nucleic acid molecule of claim 3, wherein the molecule is a plant transformation vector.

8. A prokaryotic cell comprising the nucleic acid molecule of claim 1.

9. A eukaryotic cell comprising the nucleic acid molecule of claim 1.

10. A plant cell comprising the nucleic acid molecule of claim 1, wherein the heterologous promoter is functional in the plant cell.

11. A transgenic plant comprising the nucleic acid molecule of claim 4.

12. A seed of the transgenic plant of claim 11, wherein the seed comprises the polynucleotide.

13. A commodity product produced from the transgenic plant of claim 11, wherein the commodity product comprises a detectable amount of the polynucleotide.

14. The plant cell of claim 10, wherein the cell is a *Zea mays*cell, a *Glycine max*cell, or a cell from a *Gossypium* sp.

15. The transgenic plant of claim 11, wherein the plant is maize, soybean, or cotton.

16. A method for controlling a *Euschistus heros* insect pest population, the method comprising feeding an insect pest of the population with an agent comprising the dsRNA molecule of claim 5.

17. The method according to claim 16, wherein the insect pest of the population is a male pest.

18. The method according to claim 16, wherein the insect pest of the population is a female pest.

19. The method according to claim 16, wherein the agent is a transgenic host plant of *Euschistus heros*, or a part thereof, wherein the dsRNA is expressed in the host plant or part thereof.

20. The method according to claim 16, wherein the agent is a sprayable formulation.

21. A method for improving the yield of a crop, the method comprising:
cultivating in the crop the transgenic plant of claim 11.

22. The method according to claim 21, wherein the transgenic plant is a corn plant.

23. A method for producing a transgenic plant cell, the method comprising:
transforming a plant cell with the nucleic acid molecule of claim 3;
culturing the transformed plant cell under conditions sufficient to allow for development of a plant cell culture comprising a plurality of plant cells comprising the polynucleotide;
and
selecting a transgenic plant cell that comprises the polynucleotide and expresses the dsRNA molecule encoded by the polynucleotide.

24. A method for producing a hemipteran pest-resistant transgenic plant, the method comprising:
regenerating a transgenic plant from the plant cell of claim 10.

25. The nucleic acid molecule of claim 1, further comprising a polynucleotide encoding an insecticidal polypeptide from *Bacillus thuringiensis* or a PIP-1polypeptide.

26. The nucleic acid of claim 25, wherein the polynucleotide encodes an insecticidal polypeptide from *B. thuringiensis* that is selected from a group comprising Cry1A, Cry2A, Cry3A, Cry11A, and Cry51A.

27. The plant cell of claim 10, wherein the plant cell comprises a polynucleotide encoding an insecticidal polypeptide from *Bacillus thuringiensis* or a PIP-1 polypeptide.

28. The plant cell of claim 27, wherein the polynucleotide encodes an insecticidal polypeptide from *B. thuringiensis* that is selected from a group comprising Cry1A, Cry2A, Cry3A, Cry11A, and Cry51A.

29. The transgenic plant of claim 11, wherein the plant comprises a polynucleotide encoding an insecticidal polypeptide from *Bacillus thuringiensis* or a PIP-1 polypeptide.

30. The transgenic plant of claim 29, wherein the polynucleotide encodes an insecticidal polypeptide from *B. thuringiensis* that is selected from a group comprising Cry1A, Cry2A, Cry3A, Cry11A, and Cry51A.

31. The method according to claim 16, wherein the method further comprises feeding the insect pest of the population with an insecticidal polypeptide from *Bacillus thuringiensis* or a PIP-1 polypeptide.

32. The method according to claim 31, wherein the insecticidal polypeptide is an insecticidal polypeptide from *B. thuringiensis* that is selected from a group comprising Cry1A, Cry2A, Cry3A, Cry11A, and Cry51A.

* * * * *

SEQUENCE LISTING

<160> NUMBER OF SEQ ID NOS: 21

<210> SEQ ID NO 1
<211> LENGTH: 1728
<212> TYPE: DNA
<213> ORGANISM: Euschistus heros

<400> SEQUENCE: 1

| | | | | | | |
|---|---|---|---|---|---|---|
| aggagcaata | atctcaattt | ctgaattttt | ttacttaaac | cactttcatt | ctcaccggct | 60 |
| caattatagt | taaaaatcag | ctgatatatt | ttcactgata | taacccaacc | tgattaactt | 120 |
| aaacacttaa | gtaataatta | caagaattaa | cggttagaga | gttactcaaa | caaattttgt | 180 |
| aaaatcttat | caaacattga | tcgaaaagcc | acacaaatat | caactactaa | ataacatcaa | 240 |
| ccaaagtgat | tgattatcat | aaaattttgt | tgttttatta | aatgggaaaa | aaataaattt | 300 |
| ttgaaatcca | taaagagca | taggggcata | gagatgttaa | acaataaaaa | gcggaatttt | 360 |
| gcatctgtcg | gttgggtaaa | ttttacaata | tacattccaa | taataattat | tcccagagat | 420 |
| aacctaatat | caagtttcca | gtcactctga | cgtggaatca | catgttttca | tttgagaaac | 480 |
| atacacgctc | aaaatagcg | cttccatcaa | ttaaaatata | cacaacgaac | ttatactcta | 540 |
| ataataatat | ataatagaaa | acaaaataaa | tgaaatgact | ataccgaaac | cggtacatac | 600 |
| ccgtagtcgt | ttttcagta | ccttcagtaa | cccttactat | atttcaaaaa | tcataacttc | 660 |
| aattattaca | tcaatccaga | tcaagaaatt | gtactctaaa | ataagatatt | ttaaatttat | 720 |
| taatttatgt | acaataaatc | aatttcgttt | cgtaccttat | gacgttaaag | cattcaaatg | 780 |
| gtatagggca | ctggcggtac | tgtgataaaa | aaataataat | ttactaacta | aagaggtgag | 840 |
| cctccatccc | attcttcaga | aagctcttct | tcagattcag | tcattgtgag | attattatta | 900 |
| ttgttgatgt | ttttgttctt | atgcctgata | gaaagatctt | caggttcggt | ctgctcaggc | 960 |
| aacgaaaggt | acgcagggat | aacgtttaca | agagcttgcg | cttttctgtc | cctcgagtcg | 1020 |
| cacttgtgat | gcaggaggtg | gtgtctcctt | ctgaatttgg | caccgcacaa | tccgcagccg | 1080 |
| aatggttttt | ctcccttgtg | aattagagaa | tgggccttga | gctggttgga | atcagcgaac | 1140 |
| ctcgaggaac | agacttggca | agcgtaaggc | cgttctccgg | tatgtacccg | taggtgtctc | 1200 |
| ctcaagttgg | ctacttgcac | gaagtacctg | tcgcagtggt | cgcaatggta | aggcttctcg | 1260 |
| ccagtgtgtg | tgcgtatgtg | ggtgcggaga | tggtggtccc | gtcgaaacct | tctgtggcac | 1320 |
| tcggggcact | cgaacggccg | ttctccagtg | tgggttcttt | cgtgattttt | gagaacgtgc | 1380 |
| ttatgcttga | aggactggtt | acaagtgagg | cagacgaaag | ctctgtccct | cccaggagga | 1440 |
| gagtcttcgt | ccttcttctt | cctccctaca | ggctctggag | gtggagctgc | ccagagcaaa | 1500 |
| gagtgcgaga | atagggagcc | gcctccgatc | ccgtggagag | ccaaaagtcc | tggcattccg | 1560 |
| gctgccagaa | gaccggcctc | tggaccgttt | tcttctcgtt | tgcttgcttc | cttcattgtg | 1620 |
| caccttccga | cgcctactac | tgaagtcaag | ccctggttg | ggttgttggt | tgcgtgtatg | 1680 |
| agagacaagg | ccatggaggt | gttatagaga | cgaaggcatg | gcaggaac | | 1728 |

<210> SEQ ID NO 2
<211> LENGTH: 288
<212> TYPE: PRT
<213> ORGANISM: Euschistus heros

<400> SEQUENCE: 2

Met Ala Leu Ser Leu Ile His Ala Thr Asn Asn Pro Thr Lys Gly Leu
1               5                   10                  15

```
Thr Ser Val Val Gly Val Gly Arg Cys Thr Met Lys Glu Ala Ser Lys
             20                  25                  30

Arg Glu Glu Asn Gly Pro Glu Ala Gly Leu Leu Ala Ala Gly Met Pro
         35                  40                  45

Gly Leu Leu Ala Leu His Gly Ile Gly Gly Ser Leu Phe Ser His
     50                  55                  60

Ser Leu Leu Trp Ala Ala Pro Pro Glu Pro Val Gly Arg Lys Lys
65                   70                  75                  80

Lys Asp Glu Asp Ser Pro Pro Gly Arg Asp Arg Ala Phe Val Cys Leu
                 85                  90                  95

Thr Cys Asn Gln Ser Phe Lys His Lys His Val Leu Lys Asn His Glu
             100                 105                 110

Arg Thr His Thr Gly Glu Arg Pro Phe Glu Cys Pro Glu Cys His Arg
         115                 120                 125

Arg Phe Arg Arg Asp His His Leu Arg Thr His Ile Arg Thr His Thr
     130                 135                 140

Gly Glu Lys Pro Tyr His Cys Asp His Cys Asp Arg Tyr Phe Val Gln
145                 150                 155                 160

Val Ala Asn Leu Arg Arg His Leu Arg Val His Thr Gly Glu Arg Pro
                 165                 170                 175

Tyr Ala Cys Gln Val Cys Ser Ser Arg Phe Ala Asp Ser Asn Gln Leu
             180                 185                 190

Lys Ala His Ser Leu Ile His Lys Gly Glu Lys Pro Phe Gly Cys Gly
         195                 200                 205

Leu Cys Gly Ala Lys Phe Arg Arg Arg His His Leu Leu His His Lys
     210                 215                 220

Cys Asp Ser Arg Asp Arg Lys Ala Gln Ala Leu Val Asn Val Ile Pro
225                 230                 235                 240

Ala Tyr Leu Ser Leu Pro Glu Gln Thr Glu Pro Glu Asp Leu Ser Ile
                 245                 250                 255

Arg His Lys Asn Lys Asn Ile Asn Asn Asn Asn Leu Thr Met Thr
             260                 265                 270

Glu Ser Glu Glu Glu Leu Ser Glu Glu Trp Asp Gly Gly Ser Pro Leu
         275                 280                 285

<210> SEQ ID NO 3
<211> LENGTH: 434
<212> TYPE: DNA
<213> ORGANISM: Euschistus heros

<400> SEQUENCE: 3
gagcttgcgc ttttctgtcc ctcgagtcgc acttgtgatg caggaggtgg tgtctccttc      60
tgaatttggc accgcacaat ccgcagccga atggttttc tcccttgtga attagagaat      120
gggccttgag ctggttggaa tcagcgaacc tcgaggaaca gacttggcaa gcgtaaggcc     180
gttctccggt atgtacccgt aggtgtctcc tcaagttggc tacttgcacg aagtaccctgt   240 cgcagtggtc gcaatggtaa ggcttctcgc cagtgtgtgt gcgtatgtgg gtgcggagat    300
ggtggtcccg tcgaaaccct tctgtggcac tcggggcactc gaacggccgt tctccagtgt  360
gggttctttc gtgattttg agaacgtgct tatgcttgaa ggactggtta caagtgaggc    420
agacgaaagc tctg                                                       434

<210> SEQ ID NO 4
<211> LENGTH: 605
<212> TYPE: DNA
```

<213> ORGANISM: Euschistus heros

<400> SEQUENCE: 4

```
aaacattgat cgaaaagcca cacaaatatc aactactaaa taacatcaac caaagtgatt    60
gattatcata aaattttgtt gttttattaa atgggaaaaa ataaattttt tgaaatccat   120
aaaagagcat aggggcatag agatgttaaa caataaaaag cggaattttg catctgtcgg   180
ttgggtaaat tttacaatat acattccaat aataattatt cccagagata acctaatatc   240
aagtttccag tcactctgac gtggaatcac atgttttcat ttgagaaaca tacacgctca   300
aaaatagcgc ttccatcaat taaaatatac acaacgaact tatactctaa taataatata   360
taatagaaaa caaataaaat gaaatgacta taccgaaacc ggtacatacc cgtagtcgtt   420
tttacagtac cttcagtaac ccttactata tttcaaaaat cataacttca attattacat   480
caatccagat caagaaattg tactctaaaa taagatattt taaatttatt aatttatgta   540
caataaatca atttcgtttc gtaccttatg acgttaaagc attcaaatgg tatagggcac   600
tggcg                                                              605
```

<210> SEQ ID NO 5
<211> LENGTH: 20
<212> TYPE: DNA
<213> ORGANISM: Artificial Sequence
<220> FEATURE:
<223> OTHER INFORMATION: promotor oligonucleotide

<400> SEQUENCE: 5

```
taatacgact cactataggg                                               20
```

<210> SEQ ID NO 6
<211> LENGTH: 471
<212> TYPE: DNA
<213> ORGANISM: Artificial Sequence
<220> FEATURE:
<223> OTHER INFORMATION: YFP hpRNA-forming sequence

<400> SEQUENCE: 6

```
atgtcatctg gagcacttct ctttcatggg aagattcctt acgttgtgga gatggaaggg    60
aatgttgatg ccacacctt tagcatacgt gggaaaggct acggagatgc ctcagtggga   120
aaggactagt accggttggg aaaggtatgt ttctgcttct acctttgata tatatataat   180
aattatcact aattagtagt aatatagtat ttcaagtatt ttttcaaaa taaaagaatg   240
tagtatatag ctattgcttt tctgtagttt ataagtgtgt atattttaat ttataacttt   300
tctaatatat gaccaaaaca tggtgatgtg caggttgatc cgcggttact ttcccactga   360
ggcatctccg tagccttttcc cacgtatgct aaaggtgtgg ccatcaacat tcccttccat   420
ctccacaacg taaggaatct tcccatgaaa gagaagtgct ccagatgaca t            471
```

<210> SEQ ID NO 7
<211> LENGTH: 222
<212> TYPE: DNA
<213> ORGANISM: Solanum tuberosum

<400> SEQUENCE: 7

```
gactagtacc ggttgggaaa ggtatgtttc tgcttctacc tttgatatat atataataat    60
tatcactaat tagtagtaat atagtatttc aagtattttt tcaaaataa aagaatgtag   120
tatatagcta ttgcttttct gtagtttata agtgtgtata ttttaattta aacttttct   180
aatatatgac caaaacatgg tgatgtgcag gttgatccgc gg                     222
```

<210> SEQ ID NO 8
<211> LENGTH: 45
<212> TYPE: DNA
<213> ORGANISM: Artificial Sequence
<220> FEATURE:
<223> OTHER INFORMATION: Primer BSB_kr-1-F

<400> SEQUENCE: 8
ttaatacgac tcactatagg gagacagagc tttcgtctgc ctcac        45

<210> SEQ ID NO 9
<211> LENGTH: 44
<212> TYPE: DNA
<213> ORGANISM: Artificial Sequence
<220> FEATURE:
<223> OTHER INFORMATION: Primer BSB_kr-1-R

<400> SEQUENCE: 9
ttaatacgac tcactatagg gagagagctt gcgcttttct gtcc         44

<210> SEQ ID NO 10
<211> LENGTH: 47
<212> TYPE: DNA
<213> ORGANISM: Artificial Sequence
<220> FEATURE:
<223> OTHER INFORMATION: Primer BSB_kr-2-F

<400> SEQUENCE: 10
ttaatacgac tcactatagg gagacgccag tgccctatac catttga      47

<210> SEQ ID NO 11
<211> LENGTH: 47
<212> TYPE: DNA
<213> ORGANISM: Artificial Sequence
<220> FEATURE:
<223> OTHER INFORMATION: Primer BSB_kr-2-R

<400> SEQUENCE: 11
ttaatacgac tcactatagg gagaaaacat tgatcgaaaa gccacac      47

<210> SEQ ID NO 12
<211> LENGTH: 301
<212> TYPE: DNA
<213> ORGANISM: Artificial Sequence
<220> FEATURE:
<223> OTHER INFORMATION: Sense strand of YFPv2 dsRNA

<400> SEQUENCE: 12
catctggagc acttctcttt catgggaaga ttccttacgt tgtggagatg gaagggaatg        60
ttgatggcca caccttagc atacgtggga aaggctacgg agatgcctca gtgggaaagg       120
ttgatgcaca gttcatctgc acaactggtg atgttcctgt gccttggagc acacttgtca      180
ccactctcac ctatggagca cagtgctttg ccaagtatgg tccagagttg aaggacttct      240
acaagtcctg tatgccagat ggctatgtgc aagagcgcac aatcaccttt gaaggagatg      300
g                                                                     301

<210> SEQ ID NO 13
<211> LENGTH: 47
<212> TYPE: DNA
<213> ORGANISM: Artificial Sequence
<220> FEATURE:
<223> OTHER INFORMATION: Primer YFPv2-F

<400> SEQUENCE: 13
ttaatacgac tcactatagg gagagcatct ggagcacttc tctttca         47

<210> SEQ ID NO 14
<211> LENGTH: 46
<212> TYPE: DNA
<213> ORGANISM: Artificial Sequence
<220> FEATURE:
<223> OTHER INFORMATION: Primer YFPv2-R

<400> SEQUENCE: 14
ttaatacgac tcactatagg gagaccatct ccttcaaagg tgattg          46

<210> SEQ ID NO 15
<211> LENGTH: 1728
<212> TYPE: RNA
<213> ORGANISM: Euschistus heros

<400> SEQUENCE: 15
aggagcaaua aucucaauuu cugaauuuuu uuacuuaaac cacuuucauu cucaccggcu    60
caauuauagu uaaaaaucag cugauauauu uucacugaua uaacccaacc ugauuaacuu   120
aaacacuuaa guauaauua caagaauuaa cgguuagaga guuacucaaa caauuuugu    180 aaaaucuuau caaacauuga ucgaaaagcc acacaaauau caacuacuaa auaacaucaa   240
ccaaagugau ugauuaucau aaauuuugu uguuuuauua aaugggaaaa aaauaaauu    300 uugaaaucca uaaaagagca uaggggcaua gagauguuaa acaauaaaaa gcggaauuuu   360
gcaucugucg guuggguaaa uuuuacaaua uacauuccaa uaauaauuau ucccagagau   420
aaccuaauau caaguuucca gucacucuga cguggaauca caguguuuca uuugagaaac   480
auacacgcuc aaaauuagcg cuuccaucaa uuaaaauaua cacaacgaac uuauacucua   540
auaauaauau auaauagaaa acaaaauaaa ugaaaugacu uaccgaaac cgguacauac    600 ccguagucgu uuuacaguaa ccuucaguaa cccuuacuau auuucaaaaa ucauaacuuc   660
aauuauuaca ucaauccaga ucaagaaauu guacucuaaa auaagauauu uuaaauuuau   720
uaauuuaugu acaauaaauc aauuucguuu cguaccuuau gacguuaaag cauucaaaug   780
guauagggca cuggcgguac ugugauaaaa aaauaauaau uuacuaacua aagaggugag   840
ccuccauccc auucuucaga aagcucuucu ucagauucag ucauugugag auuauuauua   900
uuguugaugu uuuuguucuu augccugaua gaaagaucuu cagguucggu cugcucaggc   960
aacgaaaggu acgcagggau aacguuuaca agagcuugcg cuuuucuguc ccucgagucg  1020
cacuugugau gcaggaggug gugucuccuu cugaauuugg caccgcacaa uccgcagccg  1080
aauggguuuu cucccuugug aauuagagaa ugggccuuga gcugguugga aucagcgaac  1140
cucgaggaac agacuuggca agcguaaggc cguucccgg uauguacccg uagguguguc  1200
cucaaguugg cuacuugcac gaaguaccug ucgcaguggu cgcaauggua aggcuucucg  1260
ccagugugug ugcguaugug ggugcggaga uggugguccc gucgaaaccu ucuguggcac  1320
ucggggcacu cgaacggccg uucuccagug uggguucuuu cgugauuuuu gagaacgugc  1380
uuaugcuuga aggacugguu acaagugagg cagacgaaag cucuguccu cccaggagga  1440 gagucuucgu ccuucuucuu ccucccuaca ggcucuggag guggagcugc ccagagcaaa  1500
gagugcgaga uaggagcc gccuccgauc ccguggagag ccaaaagucc uggcauuccg  1560
gcugccagaa gaccggccuc uggaccguuu ucuucgcuu ugcuugcuuc cuucauugug  1620
caccuuccga cgccuacuac ugaagucaag cccuugguug gguuguuggu ugcguguaug  1680

```
agagacaagg ccauggaggu guuauagaga cgaaggcaug gcaggaac                 1728
```

<210> SEQ ID NO 16
<211> LENGTH: 434
<212> TYPE: RNA
<213> ORGANISM: Euschistus heros

<400> SEQUENCE: 16

```
gagcuugcgc uuucugucc cucgagucgc acuugugaug caggaggugg ugucuccuuc      60
ugaauuuggc accgcacaau ccgcagccga augguuuuuc ucccuuguga auuagagaau    120
gggccuugag cugguuggaa ucagcgaacc ucgaggaaca gacuuggcaa gcguaaggcc    180
guucuccggu auguacccgu aggugucucc ucaaguuggc acuugcacg aaguaccugu     240
cgcagugguc gcaauggtaa ggcuucucgc cagugugugu gcguaugugg gugcggagau    300
ggugguccccg ucgaaaccuu cuguggcacu cggggcacuc gaacggccgu ucccagugu    360
gggucuuuc gugauuuuug agaacgugcu uaugcuugaa ggacugguua caagugaggc     420
agacgaaagc ucug                                                      434
```

<210> SEQ ID NO 17
<211> LENGTH: 605
<212> TYPE: RNA
<213> ORGANISM: Euschistus heros

<400> SEQUENCE: 17

```
aaacauugau cgaaaagcca cacaaauauc aacuacuaaa uaacaucaac caaagugauu     60
gauuaucaua aaauuuuguu guuuuauuaa augggaaaaa aauaaauuuu ugaauuccau    120
aaagagcau aggggcauag agauguuaaa caauaaaaag cggaauuuug caucugucgg     180
uugggauaaau uuuacaauau acauuccaau aauaauuauu cccagagaua accuaauauc    240
aaguuuccag ucacucugac guggaaucac auguuuucau uugagaaaca uacacgcuca    300
aaaauagcgc uuccaucaau uaaaauauac acaacgaacu uauacucuaa uauaauauua    360
uaauagaaaa caaauaaau gaaaugacua uaccgaaacc gguacauacc cguagucguu     420
uuuacaguac cuucaguaac ccuuacuaua uuucaaaaau cauaacuuca auuauuacau    480
caauccagau caagaaauug uacucuaaaa uaagauauuu uaaauuuauu auuuaugua     540
caauaaauca auucguuuuc guaccuuaug acguuaaagc auucaaaugg uauagggcac    600
uggcg                                                                605
```

<210> SEQ ID NO 18
<211> LENGTH: 1134
<212> TYPE: DNA
<213> ORGANISM: Euschistus heros

<400> SEQUENCE: 18

```
tacaaaatgt gtgacgaaga agttgctgct ttagttgtag acaatggatc tggtatgtgc     60
aaagccggtt tcgctggaga tgatgcaccc cgagctgtat tcccatcaat tgttggcagg    120
cctagacacc aggtgtgcat ggttggaatg ggacaaaagg acagttatgt tggagacgaa    180
gcccaaagca agagaggtat cctcaccctg aaataccccca ttgaacacgg tatcatcacc    240
aactgggacg acatggaaaa gatctggcat cacaccttct acaacgagct gcgagtcgct    300
ccagaggaac ccccatcct cctgactgag gctcccctca accccaaagc caacaggag      360
aagatgaccc agatcatgtt tgagaccttc aacacccccag ccatgtatgt cgccatccag    420
```

```
gctgtactct ccctctatgc ctccggtcgt actaccggta ttgtacttga ctcaggagat    480
ggtgtctccc acaccgtacc catctatgaa ggttatgccc ttccccacgc catcctccgt    540
ctggatcttg ctggacgtga cttgactgac tatcttatga agatcctcac cgagcgtggt    600
tacagcttca ccaccaccgc tgaaagggaa atcgtcaggg acatcaagga aaaactgtgc    660
tatgtcgccc tggactttga gcaggaaatg gccaccgccg ctgcctccac ctccctggag    720
aagtcctatg aacttcccga cggtcaggtc atcaccatcg gtaacgagag gttccgttgc    780
ccagaggctc tcttccagcc ttccttcttg ggtatggaat cttgcggtat ccatgagact    840
gtctacaact ccatcatgaa gtgcgacgtt gacatcagga aggacttgta cgccaacacc    900
gtcctctccg gaggtaccac catgtaccca ggtattgctg acaggatgca gaaggaaatc    960
accgccctcg ctccttcaac catcaagatc aagatcattg ctcccccaga aggaagtac    1020 tccgtatgga tcggtggttc catcttggct tccctgtcca ccttccagca gatgtggatc    1080
tccaagcagg aatacgacga atccggccca ggcatcgtcc accgcaaatg cttc         1134
```

```
<210> SEQ ID NO 19
<211> LENGTH: 22
<212> TYPE: DNA
<213> ORGANISM: Artificial Sequence
<220> FEATURE:
<223> OTHER INFORMATION: Primer Actin-F

<400> SEQUENCE: 19
tcaaggaaaa actgtgctat gt                                              22

<210> SEQ ID NO 20
<211> LENGTH: 20
<212> TYPE: DNA
<213> ORGANISM: Artificial Sequence
<220> FEATURE:
<223> OTHER INFORMATION: Primer Actin-R

<400> SEQUENCE: 20
taccgatggt gatgacctga                                                 20

<210> SEQ ID NO 21
<211> LENGTH: 12
<212> TYPE: DNA
<213> ORGANISM: Artificial Sequence
<220> FEATURE:
<223> OTHER INFORMATION: Probe Actin-FAM

<400> SEQUENCE: 21
accgccgctg cc                                                         12
```